(12) United States Patent
Duprat

(10) Patent No.: US 9,375,477 B2
(45) Date of Patent: Jun. 28, 2016

(54) TOPICAL COMPOSITIONS OF AQUEOUS GEL TYPE IN THE FORM OF A HOMOGENEOUS SUSPENSION OF AN ACTIVE PRINCIPLE OF THE RETINOID CLASS CONTAINING AT LEAST ONE HYDROPHOBIC SILICA

(71) Applicant: GALDERMA RESEARCH & DEVELOPMENT, Biot (FR)

(72) Inventor: Agnès Duprat, Mougins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/404,920

(22) PCT Filed: May 30, 2013

(86) PCT No.: PCT/EP2013/061185
§ 371 (c)(1),
(2) Date: Dec. 1, 2014

(87) PCT Pub. No.: WO2013/178745
PCT Pub. Date: Dec. 5, 2013

(65) Prior Publication Data
US 2015/0150974 A1     Jun. 4, 2015

Related U.S. Application Data

(60) Provisional application No. 61/654,675, filed on Jun. 1, 2012.

(30) Foreign Application Priority Data

Jun. 1, 2012 (FR) ...................... 12 55113

(51) Int. Cl.
*A61K 47/02* (2006.01)
*A61K 31/40* (2006.01)
*A61K 8/25* (2006.01)
*A61K 31/402* (2006.01)
*A61Q 19/00* (2006.01)
*A61Q 17/04* (2006.01)
*A61Q 19/08* (2006.01)
*A61K 8/67* (2006.01)
*A61K 8/81* (2006.01)
*A61K 8/04* (2006.01)

(52) U.S. Cl.
CPC ............... *A61K 47/02* (2013.01); *A61K 8/042* (2013.01); *A61K 8/25* (2013.01); *A61K 8/671* (2013.01); *A61K 8/8158* (2013.01); *A61K 31/40* (2013.01); *A61K 31/402* (2013.01); *A61Q 19/00* (2013.01); *A61Q 19/005* (2013.01); *A61Q 17/04* (2013.01); *A61Q 19/08* (2013.01)

(58) Field of Classification Search
None
See application file for complete search history.

(56) References Cited

FOREIGN PATENT DOCUMENTS

| DE | 19946184 A1 | 3/2001 |
| WO | 2006/066978 A1 | 6/2006 |

OTHER PUBLICATIONS

English Translation of International Search Report dated Jul. 12, 2013 corresponding to International Patent Application No. PCT/EP2013/061185, 2 pages.

*Primary Examiner* — Samantha Shterengarts
(74) *Attorney, Agent, or Firm* — Dentons US LLP

(57) ABSTRACT

Aqueous-gel type topical compositions are described. The compositions can be in the form of a homogeneous suspension of an active principle of the class of retinoids including at least one hydrophobic silica, the active principle preferably having general formula (I), and more specifically being 3"-tert-butyl-4'-(2-hydroxy-ethoxy)-4"-pyrrolidin-1-yl-[1,1'3',1"]-terphenyl-4-carboxylic acid. Also described, is the preparation mode thereof and the use of same in the treatment of dermatological conditions.

31 Claims, 5 Drawing Sheets

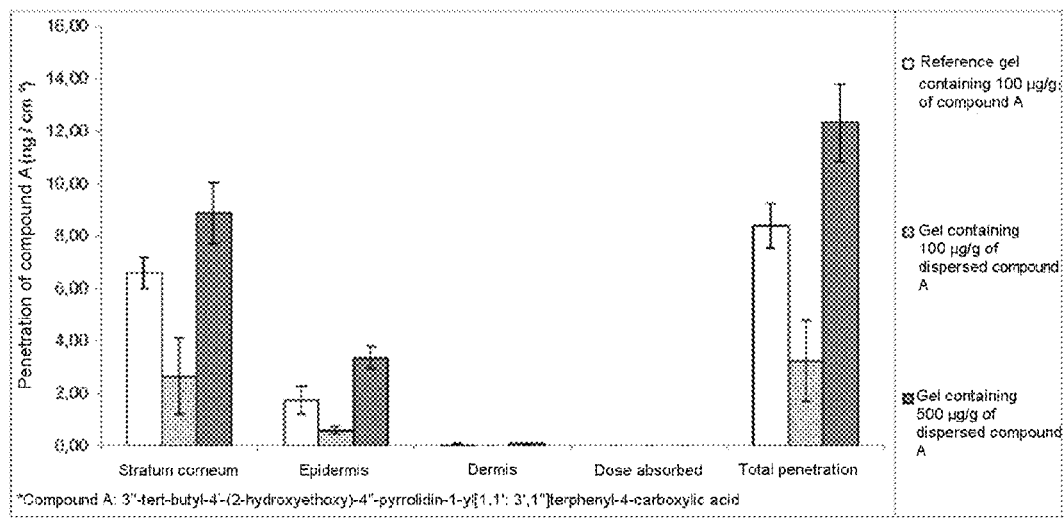
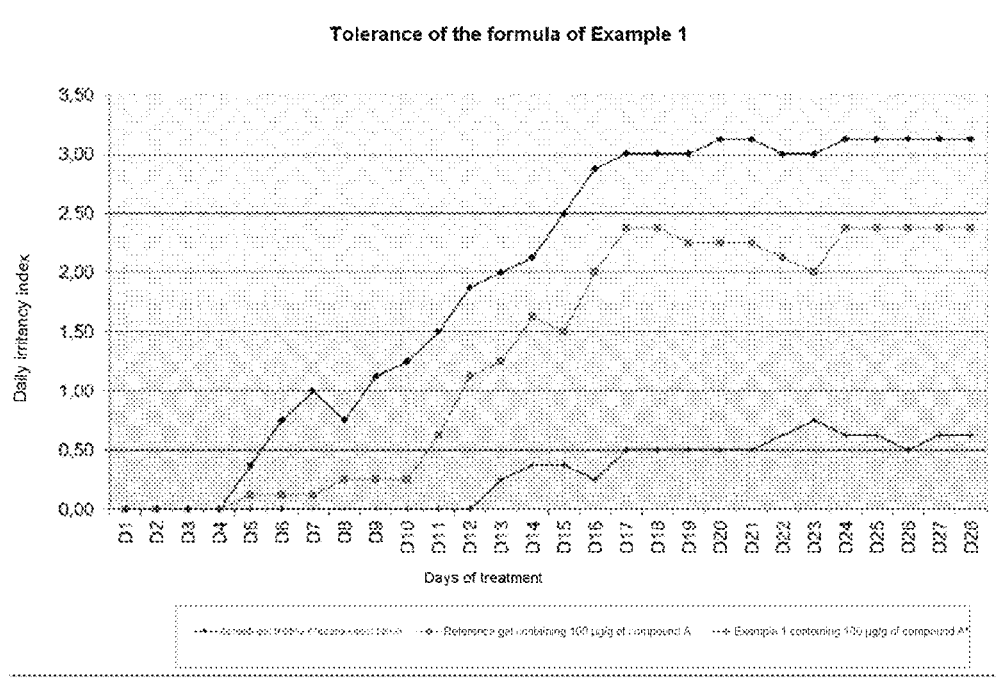
*Compound A: 3''-tert-butyl-4'-(2-hydroxyethoxy)-4''-pyrrolidin-1-yl[1,1'; 3',1'']terphenyl-4-carboxylic acid

TOPICAL COMPOSITIONS OF AQUEOUS GEL TYPE IN THE FORM OF A HOMOGENEOUS SUSPENSION OF AN ACTIVE PRINCIPLE OF THE RETINOID CLASS CONTAINING AT LEAST ONE HYDROPHOBIC SILICA

CROSS-REFERENCE TO PRIOR APPLICATIONS

This application is a National Stage of PCT/EP2013/061185, filed May 30, 2013, and designating the United States (published Dec. 5, 2013, as WO 2013/178745 A1), which claims priority under 35 U.S.C. §119 to U.S. Provisional Application No. 61/654,675, filed Jun. 1, 2012, and French Patent Application No. 1255113, filed Jun. 1, 2012, each hereby expressly incorporated by reference in its entirety and each assigned to the assignee hereof.

The present invention relates to topical compositions of aqueous gel type in the form of a homogeneous suspension of an active principle of the retinoid class containing at least one hydrophobic silica, to the method for preparing them and to the use thereof for treating dermatological pathologies.

Retinoids are used in the treatment of many dermatological pathologies and prove to be especially effective in the treatment of dermatoses such as acne and psoriasis.

However, the topical application of retinoids can cause skin irritation, dryness and erythema.

The use of a galenical form in the form of an aqueous gel in which the retinoid is in dispersed form appears to be an advantageous approach for attempting to minimize irritation by virtue of a slow and sustained release of the retinoid from its dispersed form, which could lead to gradual penetration into the skin.

However, producing this type of homogeneous suspension under the usual formulation conditions has presented many drawbacks, which have not make it possible to obtain the expected homogeneous suspension.

Usually, suspensions, i.e. dispersions of an insoluble and finely divided solid in a liquid medium, are prepared using wetting agents or dispersants and/or agents that are non-solvents for the active principle. These agents allow the active principle particles to be homogeneously dispersed and to be kept in suspension in the pharmaceutical composition.

Now, the use of one of these agents alone, or of a mixture of wetting agents and of non-solvent for the retinoid used, did not make it possible to obtain a homogeneous suspension, i.e. good dispersion of the retinoid particles in the liquid medium. This implementation rather led either to partial dissolution of the retinoid or to the formation of agglomerates, or to physical instability of the composition.

There was thus a need to find a technical means for preparing such a homogeneous suspension of an active principle of the retinoid class in an aqueous gel and to evaluate the physical stability, penetration, efficacy and tolerance thereof.

It has been found, entirely unexpectedly, that the use of a hydrophobic silica makes it possible to solve this problem and to obtain homogeneous suspensions of an active principle of the retinoid class in an aqueous gel, thus having good physical stability, good chemical stability and good cutaneous tolerance.

The way in which the hydrophobic silica is used in the process for preparing these homogeneous suspensions is also particular and a determining factor for obtaining the desired result. The process for preparing these compositions thus constitutes part of the invention.

This invention, which will now be presented below, applies to any active principle of the retinoid class, more particularly to those described in patent application WO 2006/0 066 978 and even more particularly to 3"-tert-butyl-4'-(2-hydroxyethoxy)-4"-pyrrolidin-1-yl-[1,1';3',1"]-terphenyl-4-carboxylic acid.

SUMMARY OF THE INVENTION

A first subject according to the invention relates to a pharmaceutical composition comprising:
a) an active principle of the retinoid class,
b) at least one gelling agent,
c) at least one hydrophobic silica, and
d) water.

Advantageously, the composition according to the invention may also comprise at least one preserving agent.

A second subject according to the invention relates to a process for preparing a pharmaceutical composition as described previously, comprising the following steps:
a) a first step of adding from 20% to 80% by weight of the total amount of the gelling agent to the total amount of water,
b) a second step of premixing in the solid state the active principle of the retinoid class with at least one hydrophobic silica,
c) a third step, at room temperature and with homogenization, of addition of the premix obtained in step b) to the liquid gel obtained in step a), and finally
d) a fourth step of addition, with homogenization, of the remaining amount of gelling agent to the medium obtained in step c).

When the composition also contains one or more preserving agents, they are advantageously dissolved in the water before step a) of adding part of the gelling agent.

A third subject according to the invention relates to a pharmaceutical composition as described above, for its use as a medicament.

A fourth subject according to the invention relates to a pharmaceutical composition as described above for its use in treating dermatological pathologies associated with a keratinization disorder relating to cell differentiation or proliferation.

A fifth subject according to the invention relates to a pharmaceutical composition as described above for its use in treating dermatological pathologies as defined above and chosen from the group comprising:
1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;
2) keratinization disorders, in particular ichthyosis, ichthyosiform conditions, lamellar ichthyosis, Darier's disease, palmoplantar keratoderma, leukoplakia, pityriasis rubra pilaris and leukoplakiform conditions, cutaneous or mucosal (buccal) lichen;
3) dermatological conditions with an inflammatory immunoallergic component, with or without a cell proliferation disorder, and in particular all forms of psoriasis, whether cutaneous, mucosal or ungual, and even psoriatic arthritis, or else atopic dermatitis and the various forms of eczema;
4) skin disorders caused by exposure to UV radiation, and also for repairing or combating skin aging, whether it is photo-induced or chronological, or for reducing actinic keratoses and pigmentations, or any pathological conditions associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;
6) dermatological disorders such as immune dermatoses, for instance lupus erythematosus, bullous immune diseases and collagen diseases, such as scleroderma;
7) stigmata of epidermal and/or dermal atrophy induced by local or systemic corticosteroids, or any other form of cutaneous atrophy;
8) cicatrization disorders, or for preventing or repairing stretch marks, or else for promoting cicatrization;
9) in the treatment of any condition of fungal origin at the cutaneous level, such as tinea pedis and tinea versicolor;
10) pigmentation disorders, such as hyperpigmentation, melasma, hypopigmentation or vitiligo;
11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

The invention will be described in greater detail in the description and the examples which follow, and also in the appended figures, in which:

FIG. 5 illustrates the distribution profiles in the various skin compartments of gels according to the invention relative to a reference gel.

FIG. 6 illustrates the tolerance profile of a composition according to the invention relative to a reference gel and to a comparative composition.

DETAILED DESCRIPTION OF THE INVENTION

The Applicant has thus discovered, surprisingly, that the use of an effective amount of hydrophobic silica makes it possible to obtain a homogeneous suspension of an active principle of the retinoid class in a liquid medium in the form of an aqueous gel in the absence of wetting agents or dispersants.

The term "aqueous gel" means a semi-solid galenical form which contains a gelling agent for giving consistency to a solution or a hydrophilic colloidal dispersion. A gel may contain particles in suspension.

The term "suspension" means the dispersion of an insoluble, or virtually insoluble, and finely divided solid (i.e. the active principle of the retinoid class) in a liquid or semi-solid medium. It is consequently a heterogeneous device consisting of a liquid outer continuous phase and of a solid inner phase in the form of particles.

Usually, dispersions of active principles are made using wetting agents, dispersants or agents that are non-solvents for the active principle. These agents usually allow the active principle particles to be homogeneously dispersed and to be kept in suspension in the pharmaceutical composition.

Contrary to the result expected by a person skilled in the art, the use of these agents, alone or in combination, did not make it possible to obtain a homogeneous suspension of an active principle of the retinoid class in a liquid medium in the form of an aqueous gel.

By way of illustration, the use of Marcol 152 as non-solvent (lipophilic) agent for 3"-tert-butyl-4'-(2-hydroxyethoxy)-4"-pyrrolidin-1-yl-[1,1';3',1"]-terphenyl-4-carboxylic acid, taken as an example of an active principle of the retinoid class, did not make it possible to obtain a homogeneous suspension in the aqueous gel described in Table 1.

TABLE 1

| TRADE NAME | INCI NAME | % |
|---|---|---|
| Micronized 3"-tert-butyl-4'-(2-hydroxyethoxy)-4"-pyrrolidin-1-yl-[1,1';3',1"]-terphenyl-4-carboxylic acid | Micronized 3"-tert-butyl-4'-(2-hydroxyethoxy)-4"-pyrrolidin-1-yl-[1,1';3',1"]-terphenyl-4-carboxylic acid | 0.01 |
| Marcol 152 | Mineral oil | 0.20 |
| Benzoic acid | Benzoic acid | 0.10 |
| Potassium sorbate | Potassium sorbate | 0.10 |
| Simulgel 600 PHA | Acrylamide, AMPS Copolymer Dispersion 40%/Isohexadecane (Simulgel 600PHA) | 3.00 |
| Purified water | Purified water | QS 100.00 |

Figure 1:
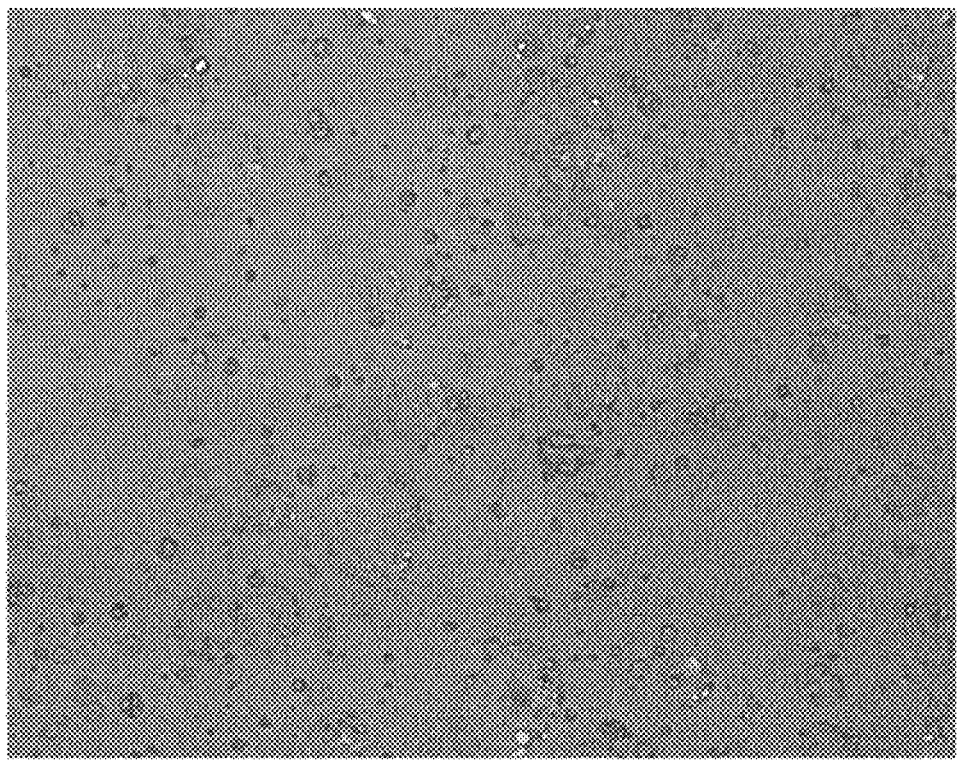
FIGS. 1 and 7 show the results of tests of direct dispersion of 3"-tert-butyl-4'-(2-hydroxyethoxy)-4"-pyrrolidin-1-yl-[1,1';3',1"]-terphenyl-4-carboxylic acid in non-solvents.

Thus, in this example, the composition obtained is not in the form of a homogeneous suspension, but rather contains agglomerates of 3"-tert-butyl-4'-(2-hydroxyethoxy)-4"-pyrrolidin-1-yl-[1,1';3',1"]-terphenyl-4-carboxylic acid between 10 and 30 µm in size. These agglomerates are located at the surface of the drops of non-solvent (lipophile) as illustrated in FIG. 1.

Surprisingly, the addition, to the composition of Table 1, of Aerosil® R972 as hydrophobic silica made it possible to obtain a homogeneous dispersion in the aqueous gel described in Table 2.

TABLE 2

| TRADE NAME | INCI NAME | % |
|---|---|---|
| Micronized 3"-tert-butyl-4'-(2-hydroxyethoxy)-4"-pyrrolidin-1-yl-[1,1';3',1"]-terphenyl-4-carboxylic acid | Micronized 3"-tert-butyl-4'-(2-hydroxyethoxy)-4"-pyrrolidin-1-yl-[1,1';3',1"]-terphenyl-4-carboxylic acid | 0.01 |
| Aerosil ® R972 | Colloidal anhydrous silica | 0.0025 |
| Marcol 152 | Mineral oil | 0.20 |
| Benzoic acid | Benzoic acid | 0.08 |
| Potassium sorbate | Potassium sorbate | 0.08 |
| Simulgel 600 PHA | Acrylamide, AMPS Copolymer Dispersion 40%/Isohexadecane/Polysorbate 80 | 3.00 |
| Purified water | Purified water | QS 100.00 |

Figure 2:
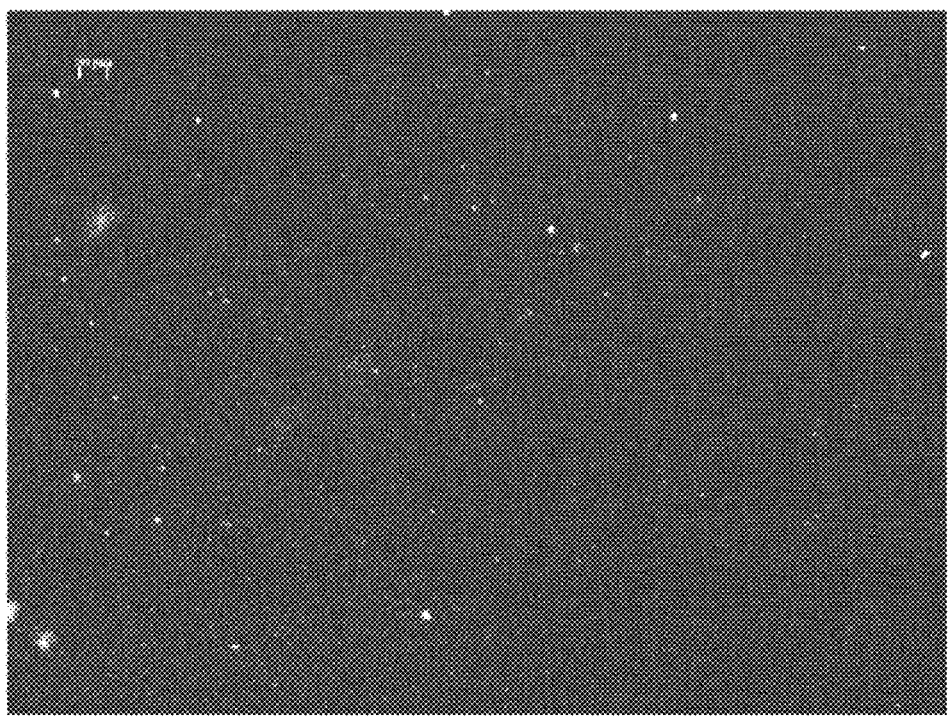
FIGS. 2, 4 and 10 show the microscopic appearance of compositions according to the invention.

Under these conditions, the composition obtained now has a 3"-tert-butyl-4'-(2-hydroxyethoxy)-4"-pyrrolidin-1-yl-[1,1';3',1"]-terphenyl-4-carboxylic acid particle size less than that obtained previously, of between 2 and 10 µm, and in the form of a homogeneous suspension as illustrated in FIG. 2. Similarly, by way of illustration, the use of Pluronic L44, as wetting agent or dispersant, in combination with glycerol and ST-cyclomethicone-5, as non-solvent agent for 3"-tert-butyl-4'-(2-hydroxyethoxy)-4"-pyrrolidin-1-yl-[1,1';3',1"]-terphenyl-4-carboxylic acid, taken as an example of an active principle of the retinoid class, did not make it possible to obtain a homogeneous suspension in the aqueous gel described in Table 3.

TABLE 3

| TRADE NAME | INCI NAME | % |
| --- | --- | --- |
| Micronized 3"-tert-butyl-4'-(2-hydroxyethoxy)-4"-pyrrolidin-1-yl-[1,1';3',1"]-terphenyl-4-carboxylic acid | Micronized 3"-tert-butyl-4'-(2-hydroxyethoxy)-4"-pyrrolidin-1-yl-[1,1';3',1"]-terphenyl-4-carboxylic acid | 0.01 |
| Pluronic L44 | Poloxamer 124 | 0.10 |
| Glycerol | Glycerol | 1.00 |
| ST-cyclomethicone-5 | Cyclopentasiloxane | 2.00 |
| Ronacare allantoin | Allantoin | 0.20 |
| Simulgel 600 PHA | Acrylamide, AMPS Copolymer Dispersion 40%/Isohexadecane (Simulgel 600PHA) | 2.00 |
| Purified water | Purified water | QS 100.00 |

Figure 3:
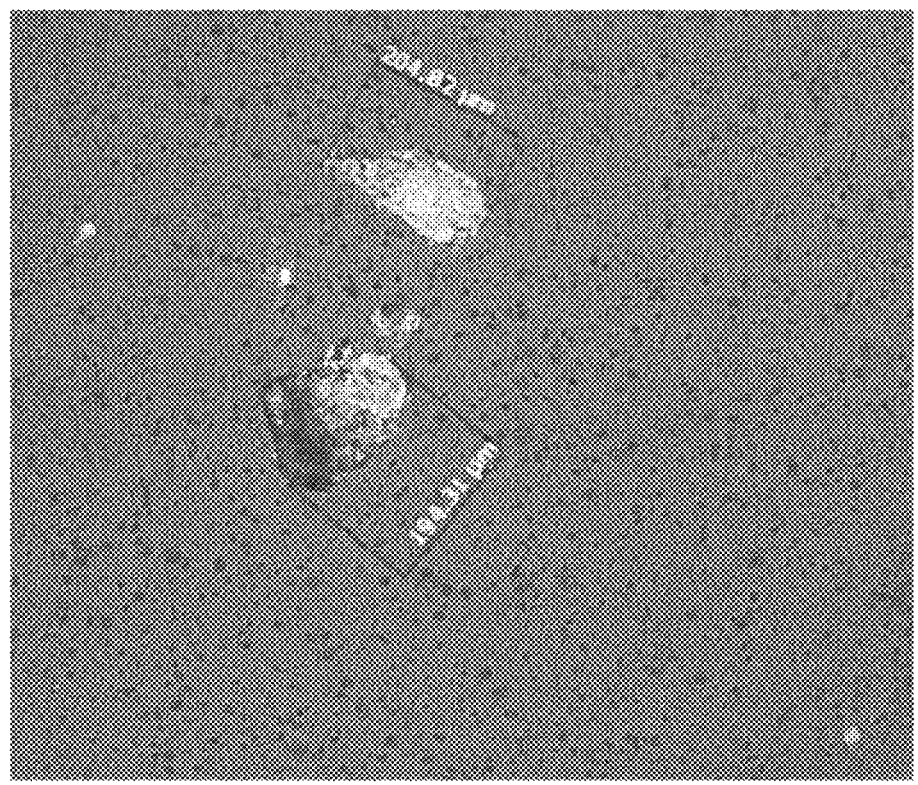
FIGS. 3, 8 and 9 show the results of tests of direct dispersion of 3"-tert-butyl-4'-(2-hydroxyethoxy)-4"-pyrrolidin-1-yl-[1,1';3',1"]-terphenyl-4-carboxylic acid in wetting agents.

Thus, in this example, the composition obtained is not in the form of a homogeneous suspension, but rather contains agglomerates of 3"-tert-butyl-4'-(2-hydroxyethoxy)-4"-pyrrolidin-1-yl-[1,1';3',1"]-terphenyl-4-carboxylic acid between 10 and 250 μm in size as illustrated in FIG. 3.

Surprisingly, the addition, to the composition of Table 1, of Aerosil® R972 as hydrophobic silica, instead of the combination of dispersant/non-solvent agents, made it possible to obtain a homogeneous suspension in the aqueous gel described in Table 4.

TABLE 4

| TRADE NAME | INCI NAME | % |
| --- | --- | --- |
| Micronized 3"-tert-butyl-4'-(2-hydroxyethoxy)-4"-pyrrolidin-1-yl-[1,1';3',1"]-terphenyl-4-carboxylic acid | Micronized 3"-tert-butyl-4'-(2-hydroxyethoxy)-4"-pyrrolidin-1-yl-[1,1';3',1"]-terphenyl-4-carboxylic acid | 0.008 |
| Aerosil ® R972 | Colloidal anhydrous silica | 0.002 |
| Benzoic acid | Benzoic acid | 0.06 |
| Potassium sorbate | Potassium Sorbate | 0.06 |
| Simulgel 600 PHA | Acrylamide, AMPS Copolymer Dispersion 40%/Isohexadecane/Polysorbate 80 | 3.00 |
| Purified water | Purified water | QS 100.00 |

Figure 4:
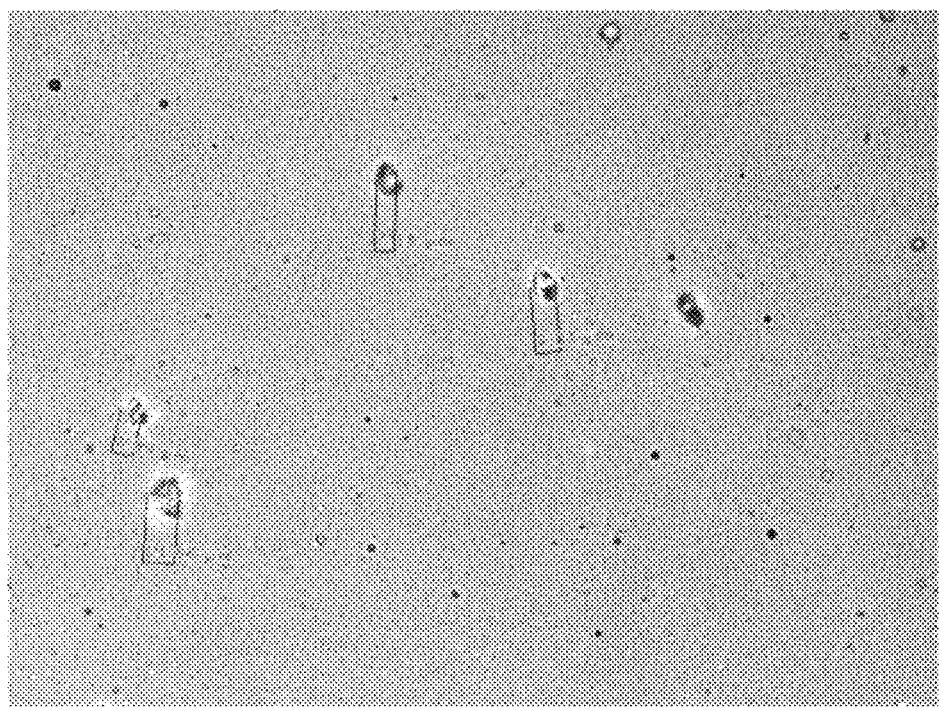

Under these conditions, the composition obtained now has a 3"-tert-butyl-4'-(2-hydroxyethoxy)-4"-pyrrolidin-1-yl-[1,1';3',1"]-terphenyl-4-carboxylic acid particle size less than that obtained previously, of between 2 and 10 μm, and in the form of a homogeneous suspension as illustrated in FIG. 4.

Thus, a first subject according to the invention concerns a pharmaceutical composition comprising:
a) an active principle of the retinoid class,
b) at least one gelling agent,
c) at least one hydrophobic silica, and
d) water.

A particular embodiment according to the first subject of the invention concerns a pharmaceutical composition comprising:
a) an active principle of the retinoid class,
b) at least one lipophilic non-solvent for the active principle,
c) at least one gelling agent,
d) at least one hydrophobic silica, and
e) water.

This composition may also comprise at least one preserving agent.

Active Principle of the Retinoid Class

The term "active principle of the retinoid class" means any type of retinoid. Examples of retinoids that may be mentioned include tretinoin, also known as retinoic acid or all-trans-retinoic acid, isotretinoin, also known as 13-cis-retinoic acid, adapalene, tazarotene, retinol, retinaldehyde or any retinoid as described in patent application WO 2006/0 066 978.

Among these compounds, it is preferred to use those described in patent application WO 2006/0 066 978 and represented by the general formula (I) below:

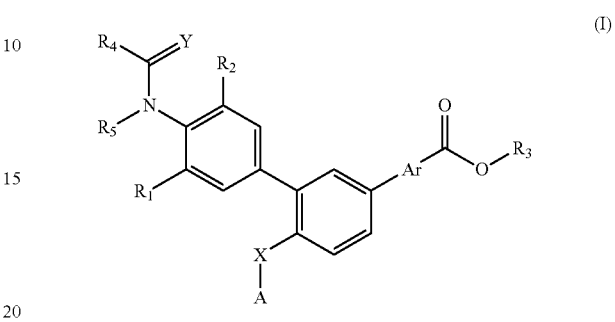

wherein
$R_1$ is a hydrogen atom, an alkyl radical containing from 1 to 4 carbon atoms or a —$CF_3$ radical;
$R_2$ is a hydrogen atom, an alkyl or alkoxy radical containing from 1 to 4 carbon atoms or a chlorine atom;
$R_3$ is a hydrogen atom, a linear or branched alkyl or alkoxy radical containing from 1 to 10 carbon atoms and preferably 1 to 6 carbon atoms optionally substituted with a methoxy group, or a linear or branched alkyl radical containing from 1 to 10 carbon atoms and preferably 1 to 6 carbon atoms, containing an ether function;
$R_4$ is a hydrogen atom or an alkyl radical containing from 1 to 3 carbon atoms;
$R_5$ is a hydrogen atom or an alkyl radical containing from 1 to 3 carbon atoms;
or else $R_4$ and $R_5$ form, together with the —N—C(=Y)— bond, a ring of pyrrolidine, pyrrolidinone, piperidine or piperidinone type;
Y represents two hydrogen atoms or a heteroatom such as oxygen or sulfur;
Ar represents a 1,4-phenyl, 2,5-pyridyl, 5,2-pyridyl or 2,5-thiophenyl ring;
X represents an oxygen atom optionally substituted with an alkyl or alkylamine chain or a C—C single bond;
A represents a hydrogen atom or the formula below:

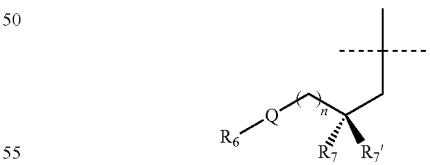

wherein
Q is an oxygen atom or an —NH— bond;
$R_6$ represents a hydrogen atom, an alkyl radical containing from 1 to 6 carbon atoms, a cycloalkyl radical containing from 3 to 6 carbon atoms, or a radical —C(O)CH3 or —C(O)CH2CH3;
$R_7$ and $R_7'$ represent, independently of one another, a hydrogen atom or a hydroxyl group, on condition that $R_7$ and $R_7'$ are not simultaneously a hydroxyl group;
n is 0, 1, 2, 3, 4 or 5;

and salts of the compounds of formula (I) when $R_3$ represents a hydrogen atom, and also the geometrical isomers of said compounds of formula (I).

Among these compounds, it is preferred to use 3"-tert-butyl-4'-(2-hydroxyethoxy)-4"-pyrrolidin-1-yl-[1,1';3',1"]-terphenyl-4-carboxylic acid in the compositions of the present invention.

In the compositions of the present invention, the active principle of the retinoid class is preferably used at concentrations ranging from 0.00001% to 5% by weight and preferentially from 0.005% to 1% by weight relative to the total weight of the composition.

Lipophilic Non-Solvent Agent

In the invention, the compositions may contain one or more lipophilic non-solvents for the active principle of the retinoid class.

The lipophilic solvent(s) may be chosen from liquid mineral oils, for instance the products Marcol 152 or Primol 352, perhydrosqualene, sold, for example, under the name Cosbiol, cyclomethicones, for instance ST Cyclomethicone-5, Q7 79120 Silicone Fluid 100 cSt, and dimethicones, for instance Fluid DC 225 10 cSt.

The lipophilic non-solvent(s) are preferably used at concentrations ranging from 0.1% to 20% by weight and preferentially from 0.1% to 5% by weight relative to the total weight of the composition.

Gelling Agent

The term "gelling agent" is intended to mean a polymer compound capable of conferring on the composition the texture of a gel.

The gelling agent(s) can in particular be chosen from polymers of vegetable origin, gums, pectins, cellulose and its derivatives, polymers of microbiological origin, such as xanthan gum, and gelling polymers of synthetic origin.

The gelling agent is more preferentially chosen from the list comprising:
- the acrylates/C10-30 alkyl acrylate crosspolymers sold under the name Pemulen TR-1 or Pemulen TR-2 by the company Lubrizol,
- gelling agents of the polyacrylamide family, such as the sodium acrylamide/acryloyldimethyl taurate copolymer/isohexadecane/polysorbate 80 mixture sold under the name Simulgel 600PHA by the company SEPPIC,
- the polyacrylamide/isoparaffin C13-14/laureth-7 mixture sold under the name Sepigel 305 by the company SEPPIC,
- the carbomers sold under the name Ultrez 20®, Ultrez 10®, Carbopol 1382® or Carbopol ETD2020NF®, Carbopol 981 or Carbopol 980 by the company Lubrizol,
- polysaccharides with, by way of nonlimiting examples, xanthan gum such as Xantural 180® sold by the company Kelco, the gellan gum sold under the name Kelcogel by the company Kelco, guar gum, cellulose and derivatives thereof, such as the microcrystalline cellulose and sodium carboxymethylcellulose sold under the name Avicel CL-611 by the company FMC Biopolymer, hydroxypropylmethylcellulose, in particular the product sold under the name Methocel E4M premium by the company Dow Chemical, or hydroxyethylcellulose, in particular the product sold under the name Natrosol HHX 250® by the company Ashland, and sodium carboxymethylcellulose, in particular Blanose cellulose gum 7F sold by the company Ashland,
- the family of aluminum magnesium silicates, such as Veegum K sold by the company Vanderbilt,
- the family of acrylic polymers coupled with hydrophobic chains such as the PEG-150/decyl/SMDI copolymer sold under the name Aculyn 44® (polycondensate comprising at least, as components, a polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)),
- the family of modified starches, such as the modified potato starch sold under the name Structure Solanace or else mixtures thereof,
- the family of carrageenans, in particular divided up into four major families: κ, λ, β, ω, such as the Viscarin® products and the Gelcarin® products sold by the company IMCD.

A gelling agent of polyacrylamide type will preferentially be used. Among the gelling agents of this type, Simulgel 600 PHA®, Sepigel 305 or Pemulen TR1 and TR2, which are known for their thickening and stabilizing properties, will be preferred.

The gelling agent(s) included in the composition according to the invention are preferably used at concentrations ranging from 0.005% to 5% by weight and preferentially from 1% to 4% by weight relative to the total weight of the composition.

Preserving Agent

The term "preserving agent" means any substance that is capable of counteracting impairment of chemical or microbiological origin of a product.

In the invention, the compositions may comprise one or more preserving agents, such as methyl paraben, propyl paraben, benzalkonium chloride, phenoxyethanol, benzyl alcohol, potassium sorbate, benzoic acid, 2-bromo-2-nitropropane-1,3-diol or Bronopol, chlorhexidine, chlorocresol and derivatives thereof, sodium benzoate, ethyl alcohol and diazolidinylurea. These preserving agents may be used alone or in combination in order to efficiently protect the formulae against any bacterial contamination.

They are used at preferential concentrations ranging from 0.01% to 5% by weight and preferentially from 0.01% to 5% by weight relative to the total weight of the composition.

Hydrophilic Silica

The composition contains one or more hydrophobic silicas. The amount of hydrophobic silica(s) is preferably between 0.0001% and 5% by weight relative to the total weight of the composition and more preferentially between 0,0001% and 1% by weight, The hydrophobic silicas used in the composition of the invention are preferably amorphous and of fumed origin. They are preferably in pulverulent form.

Advantageously, according to the present invention, the hydrophobic silica has a specific surface area (measured by the BET method) of greater than or equal to 100 m$^2$/g, even more advantageously greater than or equal to 150 m$^2$/g, even more advantageously greater than or equal to 190 m$^2$/g, even more advantageously greater than or equal to 220 m$^2$/g and even more advantageously greater than or equal to 250 m$^2$/g. The hydrophobic silica according to the present invention advantageously has a hydrocarbon-based or silicone-based coating. Preferably, the hydrophobic silica is coated with a silicone-based coating, for example of organosiloxane, polysiloxane or silicone oil. By way of example, silicas such as trimethylsiloxyl, dimethylsiloxyl or octylsiloxyl silicas and silicas coated with silicone oil may be used.

In a particular embodiment of the present invention, the hydrophobic silica has a specific surface area measured by the BET method) from 110 to 330 m$^2$/g, advantageously from 110 to 260 m$^2$/g, advantageously from 115 to 220 m$^2$/g, advantageously from 115 to 190 m$^2$/g, advantageously from 115 to 150 m$^2$/g, more advantageously from 115 to 140 m$^2$/g, more advantageously about 130 m²/g, and a mean coarseness of primary particles of less than 30 nm and advantageously between 5 and 20 nm.

The hydrophobic silica is chosen from the list comprising the silicas Aerosil® R972, R974, R104, R106, R202, R805, R812, R812S, R816, R7200, R8200, R9200 and R711 sold by Evonik and as described in Table 5 below, the hydrophobic fumed silicas HDK 13L and H2000 sold by Wacker, and mixtures of these various silicas.

TABLE 5

Hydrophobic silicas

| Aerosil ® grades | BET specific surface area [m²/g] | pH | Carbon content [Weight %] |
|---|---|---|---|
| Aerosil ® R972 | 110 ± 20 | 3.6-5.5 | 0.6-1.2 |
| Aerosil ® R974 | 170 ± 20 | 3.7-4.7 | 0.7-1.3 |
| Aerosil ® R104 | 150 ± 25 | ≥4.0 | 1.0-2.0 |
| Aerosil ® R106 | 250 ± 30 | ≥3.7 | 1.5-3.0 |
| Aerosil ® R202 | 100 ± 20 | 4.0-6.0 | 3.5-5.0 |
| Aerosil ® R805 | 150 ± 25 | 3.5-5.5 | 4.5-6.5 |
| Aerosil ® R812 | 260 ± 30 | 5.5-7.5 | 2.0-3.0 |
| Aerosil ® R812S | 220 ± 25 | 5.5-7.5 | 3.0-4.0 |
| Aerosil ® R816 | 190 ± 20 | 4.0-5.5 | 0.9-1.8 |
| Aerosil ® R7200 | 150 ± 25 | 4.0-6.0 | 4.5-6.5 |
| Aerosil ® R8200 | 160 ± 25 | ≥5.0 | 2.0-4.0 |
| Aerosil ® R9200 | 170 ± 20 | 3.4-5.0 | 0.7-1.3 |
| Aerosil ® R711 | 150 ± 25 | 4.0-6.0 | 4.5-6.5 |

In particular, the preferred silica is an Aerosil® R972 silica produced by Evonik. For the Aerosil® R972 type, a Pharma grade will be preferred, which is a hydrophobic colloidal silica (INCI: Silica Dimethyl Silylate), which is amorphous, anhydrous and of high purity, for use as an excipient in pharmaceutical products (grade tested according to the European Pharmacopoeia and according to the USP/NF monograph).

Aerosil® R972 is a hydrophobic silica obtained after treating a hydrophilic silica with DDS (dimethyldichlorosilane).

According to a particular embodiment, the first subject according to the invention concerns a pharmaceutical composition comprising:
a) an active principle of the retinoid class represented by the general formula (I)

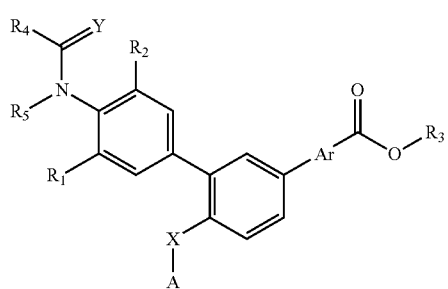

wherein
$R_1$ is a hydrogen atom, an alkyl radical containing from 1 to 4 carbon atoms or a —$CF_3$ radical;
$R_2$ is a hydrogen atom, an alkyl or alkoxy radical containing from 1 to 4 carbon atoms or a chlorine atom;
$R_3$ is a hydrogen atom, a linear or branched alkyl or alkoxy radical containing from 1 to 10 carbon atoms and preferably 1 to 6 carbon atoms optionally substituted with a methoxy group, or a linear or branched alkyl radical containing from 1 to 10 carbon atoms and preferably 1 to 6 carbon atoms, containing an ether function;
$R_4$ is a hydrogen atom or an alkyl radical containing from 1 to 3 carbon atoms;
$R_5$ is a hydrogen atom or an alkyl radical containing from 1 to 3 carbon atoms;
or else $R_4$ and $R_5$ form, together with the —N—C(=Y)— bond, a ring of pyrrolidine, pyrrolidinone, piperidine or piperidinone type;
Y represents two hydrogen atoms or a heteroatom such as oxygen or sulfur;
Ar represents a 1,4-phenyl, 2,5-pyridyl, 5,2-pyridyl or 2,5-thiophenyl ring;
X represents an oxygen atom optionally substituted with an alkyl or alkylamine chain or a C—C single bond;
A represents a hydrogen atom or the formula below:

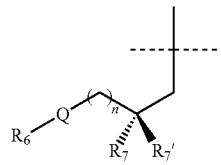

wherein
Q is an oxygen atom or an —NH— bond;
$R_6$ represents a hydrogen atom, an alkyl radical containing from 1 to 6 carbon atoms, a cycloalkyl radical containing from 3 to 6 carbon atoms, or a radical —C(O)CH3 or —C(O)CH2CH3;
$R_7$ and $R_7'$ represent, independently of one another, a hydrogen atom or a hydroxyl group, on condition that $R_7$ and $R_7'$ are not simultaneously a hydroxyl group;
n is 0, 1, 2, 3, 4 or 5;
and salts of the compounds of formula (I) when $R_3$ represents a hydrogen atom, and also the geometrical isomers of said compounds of formula (I),
b) at least one gelling agent,
c) at least one hydrophobic silica, and
d) water.

According to a particular embodiment, the first subject according to the invention concerns a pharmaceutical composition comprising:
a) 3"-tert-butyl-4'-(2-hydroxyethoxy)-4"-pyrrolidin-1-yl-[1,1';3',1"]-terphenyl-4-carboxylic acid,
b) at least one gelling agent,
c) at least one hydrophobic silica, and
d) water.

According to a particular embodiment, the first subject according to the invention concerns a pharmaceutical composition comprising:
a) from 0.00001% to 5% of an active principle of the retinoid class,
b) from 0.005% to 5% of at least one gelling agent,
c) from 0.0001% to 5% of at least one hydrophobic silica, and
d) an amount of water that is sufficient to make up to 100% of the total weight of the composition.

This composition may also comprise from 0.01% to 5% of at least one preserving agent.

According to a more particular embodiment, the first subject according to the invention concerns a pharmaceutical composition comprising:
a) from 0.0001% to 5% of an active principle of the retinoid class,
b) from 0.1% to 20% of at least one lipophilic non-solvent for the active principle, c) from 0.005% to 5% of at least one gelling agent,
d) from 0.0001% to 5% of at least one hydrophobic silica, and
e) an amount of water that is sufficient to make up to 100% of the total weight of the composition.

This composition may also comprise from 0.01% to 5% of at least one preserving agent.

According to an even more particular embodiment, the first subject according to the invention concerns a pharmaceutical composition comprising:
a) from 0.00001% to 5% of 3"-tert-butyl-4'-(2-hydroxyethoxy)-4"-pyrrolidin-1-yl-[1,1';3',1"]-terphenyl-4-carboxylic acid,
b) from 0.005% to 5% of at least one gelling agent,
c) from 0.0001% to 5% of at least one hydrophobic silica, and
d) an amount of water that is sufficient to make up to 100% of the total weight of the composition.

This composition may also comprise from 0.01% to 5% of at least one preserving agent.

The compositions according to the invention may also contain other excipients, for instance:

Humectants

The humectants are preferably chosen from the list comprising glycerol, pentylene glycol, dipropylene glycol, propylene glycol, diglycerol, sorbitol, and mixtures thereof. Their amount is between 1% and 40% by weight and preferentially between 1% and 10% by weight relative to the total weight of the composition.

Chelating Agents

The chelating agents are preferably chosen from the list comprising EDTA (ethylenediaminetetraacetic acid) and derivatives or salts thereof, dihydroglycerol, citric acid, tartaric acid and gluconolactone, and mixtures thereof.

Antioxidants

The antioxidants are preferably chosen from the list comprising vitamin E and derivatives thereof, such as DL-α-tocopherol or tocopheryl acetate, vitamin C and derivatives thereof, such as ascorbyl palmitate, butylhydroxytoluene (Nipanox BHT), and mixtures thereof.

Calmatives and/or Anti-Irritants

The calmatives and/or anti-irritants are preferably chosen from the list comprising PPG-12/SMDI copolymer (or Polyolprepolymer-2), glycyrrhetinic acid or derivatives thereof, for instance Enoxolone, hyaluronic acid and salts thereof, for instance the sodium hyaluronate sold under the trade name Hyal. NA PWD PH 15-51-45, allantoin and mixtures thereof.

The compositions according to the invention show good physical stability and good chemical stability over time.

Good physical stability corresponds to maintenance of the homogeneity of the dispersed phase over time (no sedimentation of the particles, no agglomerates, no dissolution of the particles) and also good stability of the macroscopic appearance and of the viscosity of the product over time.

The limits set for good chemical stability of the active principle over time correspond to an active principle titer of between 95% and 105% (the titer of the active agent is expressed as a relative percentage relative to the initial percentage determined at TO).

A second subject according to the invention relates to a process for preparing a pharmaceutical composition as described previously, comprising the following steps:
a) a first step of adding from 20% to 80% by weight of the total amount of the gelling agent to the total amount of water,
b) a second step of premixing in the solid state the active principle of the retinoid class with at least one hydrophobic silica,
c) a third step, at room temperature and with homogenization, of addition of the premix obtained in step b) to the liquid gel obtained in step a), and finally
d) a fourth step of addition, with homogenization, of the remaining amount of gelling agent to the medium obtained in step c).

The first step a) of the process consists in preparing a liquid gel by adding to all of the purified water between 20% and 80% by weight and preferentially between 20% and 50% by weight of all of the gelling agent so as to obtain a liquid gel.

When the composition contains preserving agents, they are dissolved in the water before adding the gelling agent(s).

In the second step b) of the process, the active principle of the retinoid class is mixed in the solid state with at least one hydrophobic silica as described previously.

Optionally, the solid mixture obtained may be dispersed in at least one lipophilic non-solvent for the active principle of the retinoid class.

Among the retinoids used in this step, it will be preferred to use those corresponding to the general formula (I) and preferentially 3"-tert-butyl-4'-(2-hydroxyethoxy)-4"-pyrrolidin-1-yl-[1,1';3',1"]-terphenyl-4-carboxylic acid.

During the third step c), the mixture obtained in step b) is added, at room temperature and with homogenization, to the liquid gel obtained in step a).

Finally, in the last step d), the remaining amount of gelling agent is added to the medium obtained in step c) so as to obtain a homogeneous suspension of an active principle of the retinoid class in a liquid medium in the form of an aqueous gel.

A particular embodiment of the second subject according to the invention thus relates to a process for preparing a pharmaceutical composition as described previously, comprising the following steps:
a) a first step of adding from 20% to 80% by weight of the total amount of the gelling agent to the total amount of water,
b) a second step of premixing in the solid state the active principle of the retinoid class with at least one hydrophobic silica, followed by dispersing the solid mixture obtained in at least one lipophilic non-solvent for the active principle of the retinoid class,
c) a third step, at room temperature and with homogenization, of adding the premix obtained in step b) to the liquid gel obtained in step a), and finally
d) a fourth step of adding, with homogenization, the remaining amount of gelling agent to the medium obtained in step c).

Thus, the pharmaceutical compositions according to the invention are prepared from a mixture of the active principle of the retinoid class, preferably in micronized form, with at least one hydrophobic silica. This premix is then either dispersed in at least one lipophilic non-solvent for the active principle of the retinoid class to obtain a homogeneous suspension, which is then added to an aqueous gel, or this premix is added directly to an aqueous gel.

The pharmaceutical compositions according to the invention are designed for their use in treating dermatological pathologies associated with a keratinization disorder relating to cell differentiation or proliferation.

These compositions contain an active principle of the retinoid class.

Retinoids are ligands that modulate the nuclear retinoic acid receptors (RARs). Compounds having activity of retinoid type are described in the literature as having activities in cell proliferation and differentiation processes. These properties give this class of compounds strong potential in the treatment or prevention of many pathologies, and more particularly in dermatology and in cancer treatment.

Many biological effects of retinoids are due to a modulation of the RARs. Retinoids find in the cytosol specific protein receptors such as cellular retinoic acid-binding protein (CRABP) and cellular retinol-binding protein (CRBP). These two proteins are characterized by high specificity and high affinity for their respective ligand, retinoic acid and retinol. They are present in a large number of cell types, although no tissue specificity exists. CRBP and CRABP are thought to play an important role in the cellular effects of retinoids: there is in particular a correlation between their presence and the tissues on which retinoids exert biological effects. At the cutaneous level, the content of CRABP is higher in the epidermis than in the dermis, which might explain the large epidermal effects of retinoic acid.

Retinoic acid first binds to CRABP in the cytosol. The CRABP-retinoic acid complex is transported (during the first 16 hours in vitro) into the nucleus, where the retinoic acid is released. It then binds to another highly specific protein receptor, the nuclear retinoic acid receptor (RAR), of which at least three types exist ($\alpha$, $\beta$ and $\gamma$). Modulation of the genome expression takes place, at the cutaneous level, after complexation to form an RAR-RXR (retinoid X receptor) heterodimer. At the cutaneous level, RAR$\gamma$ forms 90% of the epidermal RARs, whereas RXR-$\alpha$ is predominant.

There was thus a technical need for the compositions according to the invention to allow, after their topical application, firstly a release of the active principle of the retinoid class in dispersed form and secondly a targeted penetration into the epidermal layer where the nuclear retinoic acid receptors (RARs) are located.

Surprisingly, it has been shown that the compositions of the invention in the form of a homogeneous suspension of an active principle of the retinoid class in an aqueous gel penetrate in a targeted manner into the epidermis while at the same time minimizing the penetration into the dermis and systemically, which also makes it possible to reduce any risk of systemic side effects.

This targeted penetration is illustrated, by way of example, in FIG. 5 (see Example 10) for two compositions in the form of a suspension of 3"-tert-butyl-4'-(2-hydroxyethoxy)-4"-pyrrolidin-1-yl-[1,1';3',1"]-terphenyl-4-carboxylic acid in an aqueous gel.

Thus, under the conditions used and as described in Example 10, the percentage of retinoic acid that has penetrated into the epidermis and the dermis 16 hours after topical application of a composition according to the invention represents between 0.1% and 0.8% by weight of the applied dose, and preferably between 0.2% and 0.4% by weight of the applied dose.

The invention thus also relates to a pharmaceutical composition in the form of a homogeneous suspension of an active principle of the retinoid class in an aqueous gel comprising an effective amount of hydrophobic silica, in which composition the amount of active principle that has penetrated into the epidermis and the dermis 16 hours after topical application represents between 0.1% and 0.8% by weight of the applied dose, and preferably between 0.2% and 0.4% by weight of the applied amount.

Another aspect of the invention concerns a pharmaceutical composition comprising:
a) an active principle of the retinoid class,
b) at least one gelling agent,
c) at least one hydrophobic silica, and
d) water,
in which the amount of active principle that has penetrated into the epidermis and the dermis 16 hours after topical application represents between 0.1% and 0.8% by weight of the applied amount and preferentially between 0.2% and 0.4% by weight of the applied amount.

Preferably, the invention relates to a pharmaceutical composition comprising:
a) an active principle of the retinoid class represented by the general formula (I)

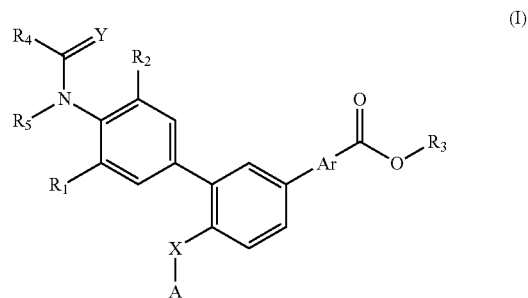

wherein
$R_1$ is a hydrogen atom, an alkyl radical containing from 1 to 4 carbon atoms or a —$CF_3$ radical;
$R_2$ is a hydrogen atom, an alkyl or alkoxy radical containing from 1 to 4 carbon atoms or a chlorine atom;
$R_3$ is a hydrogen atom, a linear or branched alkyl or alkoxy radical containing from 1 to 10 carbon atoms and preferably 1 to 6 carbon atoms optionally substituted with a methoxy group, or a linear or branched alkyl radical containing from 1 to 10 carbon atoms and preferably 1 to 6 carbon atoms, containing an ether function;
$R_4$ is a hydrogen atom or an alkyl radical containing from 1 to 3 carbon atoms;
$R_5$ is a hydrogen atom or an alkyl radical containing from 1 to 3 carbon atoms;
or else $R_4$ and $R_5$ form, together with the —N—C(=Y)— bond, a ring of pyrrolidine, pyrrolidinone, piperidine or piperidinone type;
Y represents two hydrogen atoms or a heteroatom such as oxygen or sulfur;
Ar represents a 1,4-phenyl, 2,5-pyridyl, 5,2-pyridyl or 2,5-thiophenyl ring;
X represents an oxygen atom optionally substituted with an alkyl or alkylamine chain or a C—C single bond;
A represents a hydrogen atom or the formula below:

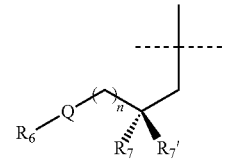

wherein
Q is an oxygen atom or an —NH— bond;
$R_6$ represents a hydrogen atom, an alkyl radical containing from 1 to 6 carbon atoms, a cycloalkyl radical containing from 3 to 6 carbon atoms, or a radical —C(O)CH3 or —C(O)CH2CH3;

R$_7$ and R$_7$' represent, independently of one another, a hydrogen atom or a hydroxyl group, on condition that R$_7$ and R$_7$' are not simultaneously a hydroxyl group;

n is 0, 1, 2, 3, 4 or 5;

and salts of the compounds of formula (I) when R$_3$ represents a hydrogen atom, and also the geometrical isomers of said compounds of formula (I), b) at least one gelling agent,
c) at least one hydrophobic silica, and
d) water, in which the amount of active principle that has penetrated into the epidermis and the dermis 16 hours after topical application represents between 0.1% and 0.8% by weight of the applied amount and preferentially between 0.2% and 0.4% by weight of the applied amount.

Even more preferably, the invention relates to a pharmaceutical composition comprising:

a) 3"-tert-butyl-4'-(2-hydroxyethoxy)-4"-pyrrolidin-1-yl-[1,1';3',1"]-terphenyl-4-carboxylic acid,
b) at least one gelling agent,
c) at least one hydrophobic silica, and
d) water, in which the amount of active principle that has penetrated into the epidermis and the dermis 16 hours after topical application represents between 0,1% and 0,8% by weight of the applied amount and preferentially between 0.2% and 0.4% by weight of the applied amount.

When compared with a reference gel in which the retinoid is dissolved, the compositions according to the invention release a percentage of retinoid about three to four times lower for an equivalent applied dose. This penetration of the active principle of the retinoid class in a lower amount into the epidermis and the dermis from the compositions in suspension form according to the invention has the advantage of minimizing the irritant effect due to this class of compounds.

This less irritant effect of the compositions according to the invention is reflected by better tolerance. The improvement of this tolerance afforded by a composition according to the invention, i.e. a pharmaceutical composition in the form of a homogeneous suspension of an active principle of the retinoid class in an aqueous gel comprising an effective amount of hydrophobic silica, is illustrated, by way of example, in FIG. 6 (see Example 11).

The irritation observed for a composition in the form of a suspension of 3"-tert-butyl-4'-(2-hydroxyethoxy)-4"-pyrrolidin-1-yl-[1,1';3',1"]-terphenyl-4-carboxylic acid in an aqueous gel as described in Example 1 is compared with that of a commercial formulation of Zorac® gel containing tazarotene and with that of a reference gel containing dissolved 3"-tert-butyl-4'-(2-hydroxyethoxy)-4"-pyrrolidin-1-yl-[1,1';3',1"]-terphenyl-4-carboxylic acid.

Thus, under the test conditions as described in Example 11, a pharmaceutical composition in the form of a homogeneous suspension of an active principle of the retinoid class in an aqueous gel comprising an effective amount of hydrophobic silica has better tolerance when compared with the commercial gel Zorac® or when compared with a gel in which the active principle of the retinoid class is dissolved. Assessment of the tolerance is measured using the daily irritancy index, the weekly irritancy index or the cumulative irritancy index.

Thus, according to another aspect, the invention relates to a pharmaceutical composition in the form of a homogeneous suspension of an active principle of the retinoid class in an aqueous gel comprising an effective amount of hydrophobic silica, for which composition the cumulative irritancy index is less than 1.5 and preferentially less than 0.5.

Another aspect of the invention concerns a pharmaceutical composition comprising:

a) an active principle of the retinoid class,
b) at least one gelling agent,
c) at least one hydrophobic silica, and
d) water, for which composition the cumulative irritancy index is less than 1.5 and preferentially less than 0.5.

Preferably, the invention relates to a pharmaceutical composition comprising:

a) an active principle of the retinoid class represented by the general formula (I)

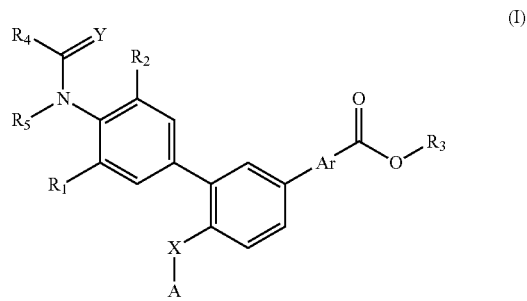

wherein

R$_1$ is a hydrogen atom, an alkyl radical containing from 1 to 4 carbon atoms or a —CF$_3$ radical;

R$_2$ is a hydrogen atom, an alkyl or alkoxy radical containing from 1 to 4 carbon atoms or a chlorine atom;

R$_3$ is a hydrogen atom, a linear or branched alkyl or alkoxy radical containing from 1 to 10 carbon atoms and preferably 1 to 6 carbon atoms optionally substituted with a methoxy group, or a linear or branched alkyl radical containing from 1 to 10 carbon atoms and preferably 1 to 6 carbon atoms, containing an ether function;

R$_4$ is a hydrogen atom or an alkyl radical containing from 1 to 3 carbon atoms;

R$_5$ is a hydrogen atom or an alkyl radical containing from 1 to 3 carbon atoms;

or else R$_4$ and R$_5$ form, together with the —N—C(=Y)— bond, a ring of pyrrolidine, pyrrolidinone, piperidine or piperidinone type;

Y represents two hydrogen atoms or a heteroatom such as oxygen or sulfur;

Ar represents a 1,4-phenyl, 2,5-pyridyl, 5,2-pyridyl or 2,5-thiophenyl ring;

X represents an oxygen atom optionally substituted with an alkyl or alkylamine chain or a C—C single bond;

A represents a hydrogen atom or the formula below:

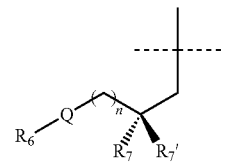

wherein

Q is an oxygen atom or an —NH— bond;

R$_6$ represents a hydrogen atom, an alkyl radical containing from 1 to 6 carbon atoms, a cycloalkyl radical containing from 3 to 6 carbon atoms, or a radical —C(O)CH3 or —C(O)CH2CH3;

$R_7$ and $R_7'$ represent, independently of one another, a hydrogen atom or a hydroxyl group, on condition that $R_7$ and $R_7'$ are not simultaneously a hydroxyl group;

n is 0, 1, 2, 3, 4 or 5;

and salts of the compounds of formula (I) when $R_3$ represents a hydrogen atom, and also the geometrical isomers of said compounds of formula (I), b) at least one gelling agent,
c) at least one hydrophobic silica, and
d) water, for which composition the cumulative irritancy index is less than 1.5 and preferentially less than 0.5.

Even more preferably, the invention relates to a pharmaceutical composition comprising:

a) 3"-tert-butyl-4'-(2-hydroxyethoxy)-4"-pyrrolidin-1-yl-[1,1';3',1"]-terphenyl-4-carboxylic acid,
b) at least one gelling agent,
c) at least one hydrophobic silica, and
d) water, for which composition the cumulative irritancy index is less than 1.5 and preferentially less than 0.5.

The compositions according to the invention have excellent chemical stability and physical stability properties.

The examples that follow are intended to illustrate the invention without in any way limiting the scope thereof.

Unless otherwise specified, the percentages indicated in the following examples are percentages by weight relative to the total weight of the composition concerned.

EXAMPLES

1—Tests of dispersion of 3"-tert-butyl-4'-(2-hydroxyethoxy)-4"-pyrrolidin-1-yl-[1,1';3',1"]-terphenyl-4-carboxylic acid using a "non-solvent"

The aim of these tests is to obtain formulations in which the active principle of the retinoid class is homogeneously dispersed in a "non-solvent" (i.e. no agglomerates or lumps, uniform size of the dispersion) and which show good physical stability (i.e. the active principle remains in its dispersed form and does not dissolve over time).

For these tests, 3"-tert-butyl-4'-(2-hydroxyethoxy)-4"-pyrrolidin-1-yl-[1,1';3',1"]-terphenyl-4-carboxylic acid is used as an example of an active principle of the retinoid class.

This retinoid is premixed in solid form with each of the non-solvents listed in Table 6 below, and this premix is added to an aqueous gel of low viscosity for the purpose of allowing easy use of the active principle and of obtaining good maintenance of the active principle in suspension (no sedimentation or agglomerates). The aqueous gel used is based on Simulgel 600.

However, none of the tests performed using a "non-solvent" for the active principle of the retinoid class made it possible to obtain a homogeneous suspension, as summarized in Table 6 below.

TABLE 6

Tests with "non-solvents" for 3"-tert-butyl-4'-(2-hydroxyethoxy)-4"-pyrrolidin-1-yl-[1,1';3',1"]-terphenyl-4-carboxylic acid.

| NON-SOLVENTS | Type of non-solvent | RESULTS |
|---|---|---|
| Purified water Glycerol | Hydrophilic agents | Unsatisfactory result (two separate phases obtained) |
| Isopropyl myristate | Lipophilic agents | The dispersion is very heterogeneous. The 3"-tert-butyl-4'-(2-hydroxyethoxy)- |

TABLE 6-continued

Tests with "non-solvents" for 3"-tert-butyl-4'-(2-hydroxyethoxy)-4"-pyrrolidin-1-yl-[1,1';3',1"]-terphenyl-4-carboxylic acid.

| NON-SOLVENTS | Type of non-solvent | RESULTS |
|---|---|---|
| Cosbiol ST-cyclomethicone 5-NF Marcol 152 Primol 352 | | 4"-pyrrolidin-1-yl-[1,1';3',1"]-terphenyl-4-carboxylic acid particles are assembled in large oil droplets that it is not possible to reduce. |

1-a) Formula with Glycerol

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.10 |
| Glycerol | Glycerol | 10.00 |
| ST-cyclomethicone 5-NF | Cyclopentasiloxane | 2.00 |
| Simulgel 600 PHA | Acrylamide, AMPS copolymer dispersion 40%/Isohexadecane/Polysorbate 80 | 2.10 |
| Purified water | Purified water | QS 100.00 |

Figure 7:
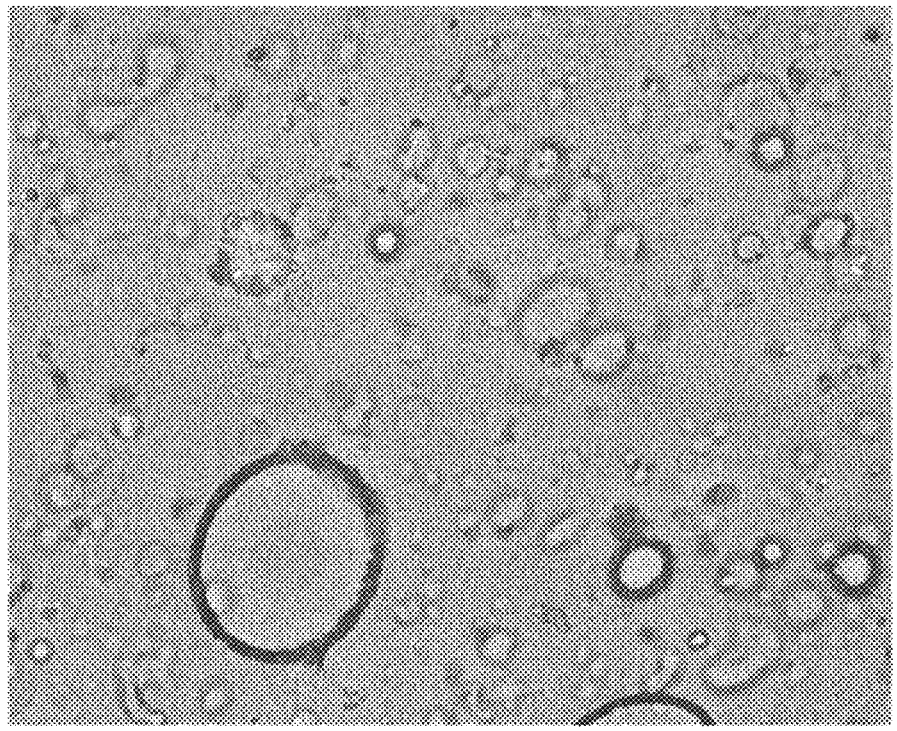

| CHARACTERIZATION At T0 | MACROSCOPIC APPEARENCE | Glossy, smooth white cream |
|---|---|---|
| | MICROSCOPIC APPEARENCE (see FIG. 7) | Heterogeneous dispersion |

1-b) Formula with Marcol 152

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid (micronized) | 3"-tert-Butyl-4'-(2-hydroxyethoxy)-4"-pyrrolidin-1-yl-[1,1';3',1"]-terphenyl-4-carboxylic acid (micronized) | 0.01 |
| Marcol 152 | Mineral oil | 0.20 |
| Benzoic acid | Benzoic acid | 0.10 |
| Potassium sorbate | Potassium sorbate | 0.10 |
| Simulgel 600 PHA | Acrylamide, AMPS copolymer dispersion 40%/Isohexadecane/Polysorbate 80 | 3.00 |
| Purified water | Purified water | QS 100.00 |

| CHARACTERIZATION At T0 | MACROSCOPIC APPEARENCE | Glossy, smooth white cream |
|---|---|---|
| | MICROSCOPIC APPEARENCE (see FIG. 1) | Heterogeneous dispersion |

These tests of direct dispersion of 3"-tert-butyl-4'-(2-hydroxyethoxy)-4"-pyrrolidin-1-yl-[1,1';3',1"]-terphenyl-4-carboxylic acid in non-solvents do not make it possible to obtain good dispersion of solid particles of the active principle of the retinoid class in an aqueous gel.

2—Tests of dispersion of 3"-tert-butyl-4'-(2-hydroxyethoxy)-4"-pyrrolidin-1-yl-[1,1';3',1"]-terphenyl-4-carboxylic acid with wetting agents For these tests, 3"-tert-butyl-4'-(2-hydroxyethoxy)-4"-pyrrolidin-1-yl-[1,1';3',1"]-terphenyl-4-carboxylic acid, used as an example of an active principle of the retinoid class, is premixed in solid form with wetting agents, alone or in combination with non-solvents:

| Wetting agents | Results |
|---|---|
| Glycerol/Propylene glycol | Poor dispersion of the active agent and partial dissolution |
| Polysorbate 60 | Dissolution of 3"-tert-butyl-4'-(2-hydroxyethoxy)-4"-pyrrolidin-1-yl-[1,1';3',1"]-terphenyl-4-carboxylic acid |
| Pluronic/Glycerol/Cyclomethicone | Very poor dispersion of the active agent. Presence of numerous aggregates |

2-a) Formula with Glycerol/Propylene Glycol

Figure 8:
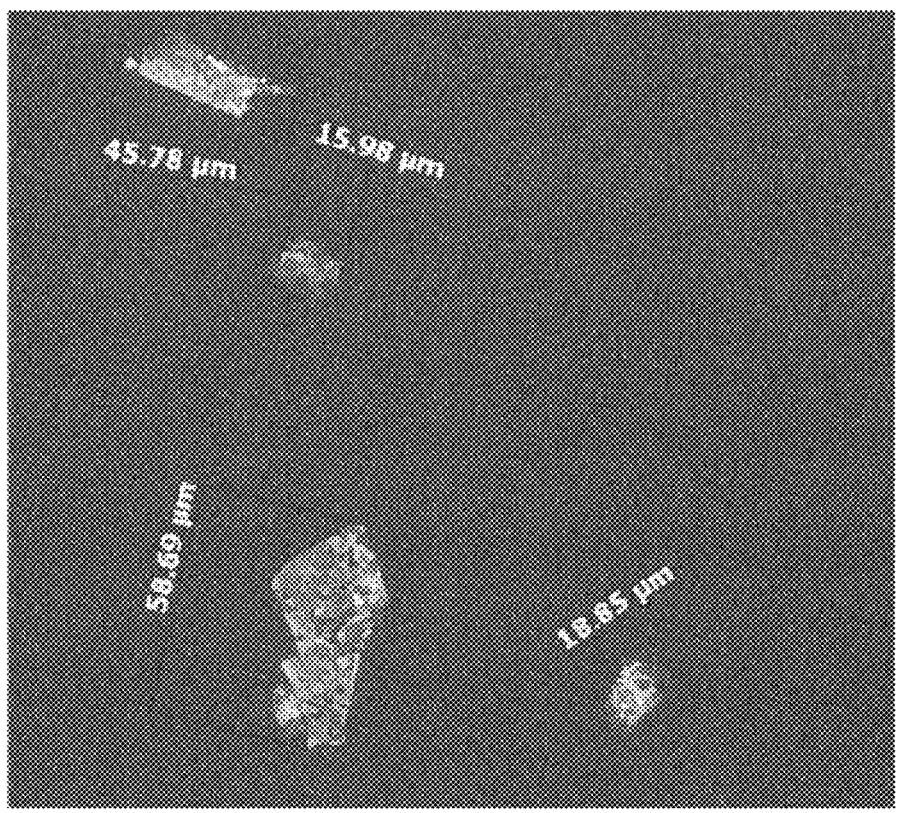

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.10 |
| Glycerol | Glycerol | 4.00 |
| Propylene glycol | Propylene glycol | 2.00 |
| Simulgel 600 PHA | Acrylamide, AMPS copolymer dispersion 40%/Isohexadecane (Simulgel 600PHA) | 4.00 |
| Purified water | Purified water | QS 100.00 |
| CHARACTERIZATION At T0 | MACROSCOPIC APPEARANCE | Glossy, smooth white cream |
| | MICROSCOPIC APPEARANCE (see FIG. 8) | Size of the heterogeneous particles 15 μm < Ø < 100 μm |

2-b) Formula with Polysorbate 60

Figure 9:
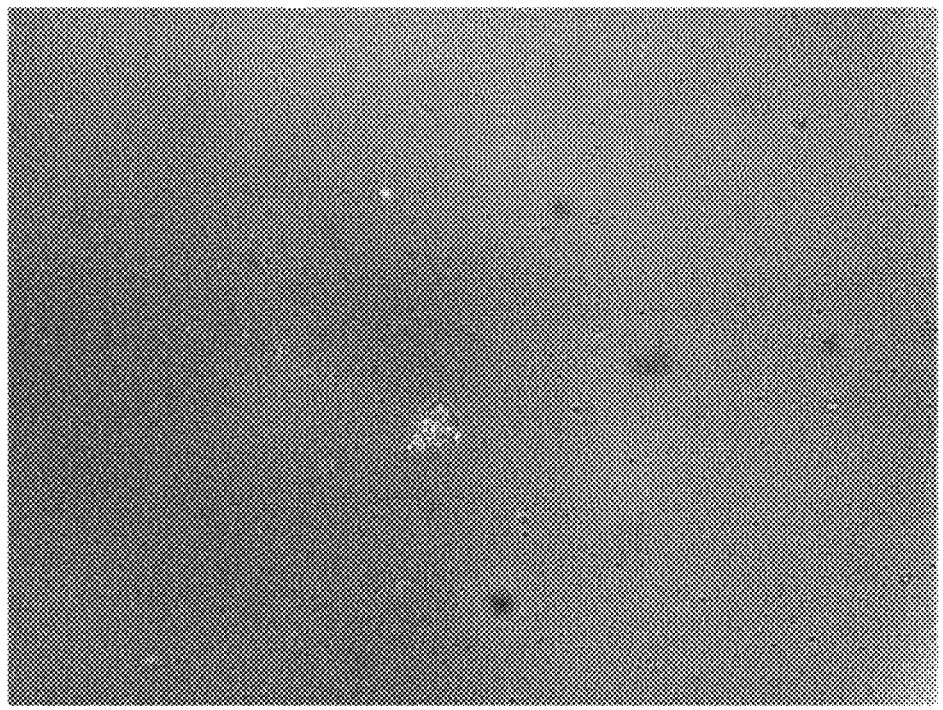

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.01 |
| Tween 60 | Polysorbate 60 | 0.09 |
| Benzoic acid | Benzoic acid | 0.10 |
| Potassium sorbate | Potassium sorbate | 0.10 |
| Simulgel 600 PHA | Acrylamide, AMPS copolymer dispersion 40%/Isohexadecane (Simulgel 600PHA) | 3.00 |
| Purified water | Purified water | QS 100.00 |
| CHARACTERIZATION At T0 | MACROSCOPIC APPEARANCE | Glossy, smooth white cream |
| | MICROSCOPIC APPEARANCE (see FIG. 9) | Very few crystals of active principle (dissolved active principle) Presence of a few agglomerates |

2-c) Formula with Pluronic/Glycerol/Cyclomethicone

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.01 |
| Pluronic L 44 | Poloxamer 124 | 0.10 |
| Glycerol | Glycerol | 1.00 |
| ST-cyclomethicone 5-NF | Cyclopentasiloxane | 2.00 |
| Ronacare allantoin | Allantoin | 0.20 |
| Simulgel 600 PHA | Acrylamide, AMPS copolymer dispersion 40%/Isohexadecane (Simulgel 600PHA) | 2.00 |
| Purified water | Purified water | QS 100.00 |
| CHARACTERIZATION At T0 | MACROSCOPIC APPEARANCE | Glossy, smooth white cream |
| | MICROSCOPIC APPEARANCE (see FIG. 3) | Presence of particles and agglomerates 10 μm < Ø < 250 μm Very heterogeneous dispersion |

These tests show that the evaluated wetting agents:
- either do not make it possible to obtain good dispersion of the particles,
- or partially dissolve the 3"-tert-butyl-4'-(2-hydroxyethoxy)-4"-pyrrolidin-1-yl-[1,1';3',1"]-terphenyl-4-carboxylic acid.

3—Examples of Formulations

In the examples that follow, the formulations prepared are characterized at T0 using the material and methods described below. The physical stability and chemical stability of the formulations are determined after storage at room temperature (RT) and +40° C. after T0+1Month and/or T0+2Months and/or T0+3Months and/or T0+6Months. 3"-tert-Butyl-4'-(2-hydroxyethoxy)-4"-pyrrolidin-1-yl-[1,1';3',1"]-terphenyl-4-carboxylic acid is used as an example of an active principle of the retinoid class.

Chemical assay of 3"-tert-butyl-4'-(2-hydroxyethoxy)-4"-pyrrolidin-1-yl-[1,1';3',1"]-terphenyl-4-carboxylic acid Material: HPLC Expression of the results: the titer of the active agent is expressed as relative % with respect to the initial % performed at T0. The limits set for good chemical stability are 95%-105%.

Macroscopic Observation:

The macroscopic observation makes it possible to guarantee the physical integrity of the products at T0 and afterwards stability.

Microscopic Observation:

The microscopic observation makes it possible to evaluate the satisfactory dispersion (homogeneity) of 3"-tert-butyl-4'-(2-hydroxyethoxy)-4"-pyrrolidin-1-yl-[1,1';3', 1"]-terphenyl-4-carboxylic acid from T0 and also the satisfactory physical stability over time (maintenance of the homogeneity of the dispersion).

Material: Zeiss Axio Microscope
pH:
Material: Mettler Toledo Seven Multi pH meter
Method: Measurements carried out at room temperature after stabilization of all the samples for 24 h in a chamber at 25° C.
Viscosity:
The viscosity measurement makes it possible to evaluate the consistency of the formulae produced.
Material: Brookfield RV DVII+Pro
Method: Measurements carried out at room temperature after stabilization of all the samples for 24 h in a chamber at 25° C. The value is read after 1 minute. The choice of the spindle and of the speed will be described in each composition example. The values obtained are expressed in centipoises (Cps).
Centrifugation:
The centrifugation makes possible to evaluate the resistance of the formulae to a mechanical stress.
Material: Galaxy 14D VWR
Method: 30 minutes at 5000 rpm

3-a) Example 1

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid (micronized) | 3"-tert-Butyl-4'-(2-hydroxyethoxy)-4"-pyrrolidin-1-yl-[1,1';3',1"]-terphenyl-4-carboxylic acid (micronized) | 0.008 |
| Aerosil ® R972 | Silica dimethyl silylate | 0.002 |
| Benzoic acid | Benzoic acid | 0.060 |
| Potassium sorbate | Potassium sorbate | 0.060 |
| Simulgel 600 PHA | Acrylamide, AMPS copolymer dispersion 40%/Isohexadecane (Simulgel 600PHA) | 3.000 |
| Purified water | Purified water | QS 100.000 |

| CHARACTERIZATION At T0 | MACROSCOPIC APPEARENCE | Glossy, smooth white cream |
|---|---|---|
| | MICROSCOPIC APPEARENCE (see FIG. 4) | Presence of particles 2 µm < Ø < 10 µm |

3-b) Example 2

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0100 |
| Aerosil ® R972 | Silica dimethyl silylate | 0.0025 |
| Benzoic acid | Benzoic acid | 0.100 |
| Potassium sorbate | Potassium sorbate | 0.100 |
| Simulgel 600 PHA | Acrylamide, AMPS copolymer dispersion 40%/Isohexadecane (Simulgel 600PHA) | 3.000 |
| Purified water | Purified water | QS 100.000 |

| CHARACTERIZATION At T0 | MACROSCOPIC APPEARENCE | Glossy, smooth white cream |
|---|---|---|
| | MICROSCOPIC APPEARENCE | Presence of particles 2 µm < Ø < 10 µm |

| MONITORING OF STABILITY | | | 1 Month | 2 Months | 3 Months | 9 Months |
|---|---|---|---|---|---|---|
| Chemical stability | Assay Initial % | RT 40° C. | 100.90 102.40 | 101.80 ND* | 99.90 100.30 | 96.8 ND* |

*ND = not done

This example shows that the described composition is chemically stable at at least 3 months at room temperature and 40° C. and at 9 months at room temperature.

3-c) Example 3

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0100 |
| Aerosil ® R972 | Silica dimethyl silylate | 0.0025 |
| Marcol 152 | Mineral oil | 0.200 |
| Benzoic acid | Benzoic acid | 0.080 |
| Potassium sorbate | Potassium sorbate | 0.080 |
| Simulgel 600 PHA | Acrylamide, AMPS copolymer dispersion 40%/Isohexadecane (Simulgel 600PHA) | 3.000 |
| Purified water | Purified water | QS 100.000 |

| CHARACTERIZATION At T0 | MACROSCOPIC APPEARENCE | Glossy, smooth white cream |
|---|---|---|
| | MICROSCOPIC APPEARENCE (see FIG. 2) | Presence of particles 2 µm < Ø < 10 µm |

3-d) Example 4

| TRADE NAME | INCI NAME | % |
|---|---|---|
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0500 |
| Aerosil ® R972 | Silica dimethyl silylate | 0.0125 |
| Marcol 152 | Mineral oil | 0.200 |
| Benzoic acid | Benzoic acid | 0.080 |
| Potassium sorbate | Potassium sorbate | 0.080 |

-continued

| Simulgel 600 PHA | Acrylamide, AMPS copolymer dispersion 40%/Isohexadecane (Simulgel 600PHA) | 3.000 |
| --- | --- | --- |
| Purified water | Purified water | QS 100.000 |

Figure 10:
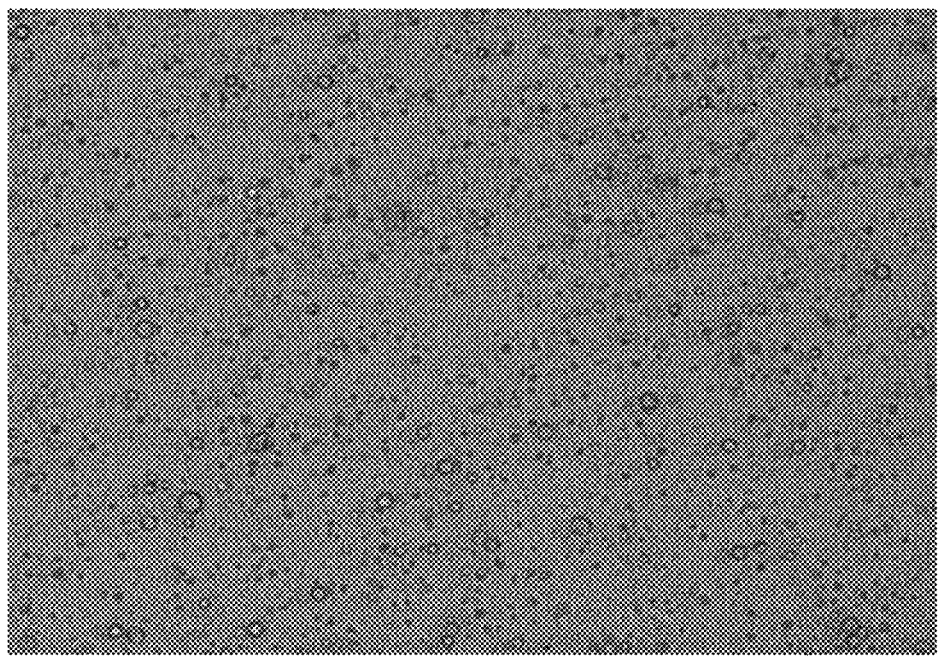

| CHARAC-TERIZATION At T0 | MACROSCOPIC APPEARENCE | Glossy, smooth white cream |
| --- | --- | --- |
| | MICROSCOPIC APPEARENCE (see FIG. 10) | Presence of particles 2 µm < Ø < 10 µm |

3-e) Example 5

| TRADE NAME | INCI NAME | % |
| --- | --- | --- |
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0500 |
| Aerosil ® R972 | Silica dimethyl silylate | 0.0125 |
| Cosbiol | Squalane | 0.500 |
| Benzalkonium chloride | Benzalkonium chloride | 0.100 |
| Pemulen TR1 | Acrylates/C10-30 alkyl acrylate crosspolymer | 0.500 |
| Purified water | Purified water | QS 100.000 |

3-f) Example 6

| TRADE NAME | INCI NAME | % |
| --- | --- | --- |
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0500 |
| Aerosil ® R972 | Silica dimethyl silylate | 0.0125 |
| Cosbiol | Squalane | 0.500 |
| Nipasol | Propylparaben | 0.050 |
| Nipagin M | Methylparaben | 0.100 |
| Pemulen TR2 | Acrylates/C10-30 alkyl acrylate crosspolymer | 0.300 |
| Purified water | Purified water | QS 100.000 |

3-g) Example 7

| TRADE NAME | INCI NAME | % |
| --- | --- | --- |
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0500 |
| Aerosil ® R972 | Silica dimethyl silylate | 0.0125 |
| Nipasol | Propylparaben | 0.050 |
| Nipagin M | Methylparaben | 0.100 |
| Pemulen TR2 | Acrylates/C10-30 alkyl acrylate crosspolymer | 0.500 |
| Purified water | Purified water | QS 100.000 |

3-h) Example 8

| TRADE NAME | INCI NAME | % |
| --- | --- | --- |
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.100 |
| Aerosil ® R972 | Silica dimethyl silylate | 0.025 |
| Benzoic acid | Benzoic acid | 0.100 |
| Potassium sorbate | Potassium sorbate | 0.100 |
| Simulgel 600 PHA | Acrylamide, AMPS copolymer dispersion 40%/Isohexadecane (Simulgel 600PHA) | 3.000 |
| Purified water | Purified water | QS 100.000 |

| CHARACTERIZATION At T0 | MACROSCOPIC APPEARENCE | Glossy, smooth white cream |
| --- | --- | --- |
| | MICROSCOPIC APPEARENCE | Presence of particles 2 µm < Ø < 10 µm |

| MONITORING OF STABILITY | | | 1 Month | 2 Months | 3 Months | 9 Months |
| --- | --- | --- | --- | --- | --- | --- |
| Chemical stability | Assay Initial % | RT 40° C. | ND* ND* | 100.80 98.30 | 101.00 102.10 | 99.90 ND* |

*ND = not done

This example shows that described composition is chemically stable at at least 3 months at room temperature and 40° C. and at 9 months at room temperature.

3-i) Example 9

| TRADE NAME | INCI NAME | % |
| --- | --- | --- |
| 3"-tert-Butyl-4'-(2-hydroxyethoxy)-4"-pyrrolidin-1-yl-[1,1';3',1"]-terphenyl-4-carboxylic acid | 3"-tert-Butyl-4'-(2-hydroxyethoxy)-4"-pyrrolidin-1-yl-[1,1';3',1"]-terphenyl-4-carboxylic acid | 0.0500 |
| Aerosil ® R972 | Silica dimethyl silylate | 0.0125 |
| Benzoic acid | Benzoic acid | 0.100 |
| Potassium sorbate | Potassium sorbate | 0.100 |
| Simulgel 600 PHA | Acrylamide, AMPS copolymer dispersion 40%/Isohexadecane (Simulgel 600PHA) | 3.000 |
| Purified water | Purified water | QS 100.000 |

| CHARAC-TERIZATION At T0 | MACROSCOPIC APPEARENCE | Glossy, smooth white cream |
| --- | --- | --- |
| | MICROSCOPIC APPEARENCE | Presence of particles 2 µm < Ø < 10 µm |

4—Example 10

In Vitro Studies of Cutaneous Penetration on Human Skin

These studies make it possible to characterize the formulations of the invention by determining in vitro the penetration of the active principle of the retinoid classes into the various skin compartments. They also make it possible to establish a classification of the formulations of the invention according to whether they will be able to promote or limit the penetration of the active principle, or target a particular skin compartment. The capacity of a formulation to make a compound penetrate is one of the key features with a view to topical application, for which the skin constitutes a major barrier.

The cutaneous penetration studies performed on the formulations of the invention containing an active principle of the retinoid class were performed in vitro on whole human abdominal skin after excision, this skin being mounted on a Franz cell.

After topical application of a given amount of the formulation to the surface of the skin, the penetration of the active principle is measured 16 hours after application.

The amount of active principle of the retinoid class is measured in the various skin compartments: stratum corneum, epidermis, dermis and also in the receiving liquid.

By way of example, the penetration of the active principle of the formulations of Examples 2 and 9 was evaluated, and the details of these penetration studies are given in the table below.

The evaluated formulations are the dispersed gels of Example 2 containing 100 µg/g of 3"-tert-butyl-4'-(2-hydroxyethoxy)-4"-pyrrolidin-1-yl-[1,1';3',1"]-terphenyl-4-carboxylic acid, and of Example 9 containing 500 µg/g of this same active principle.

| Skin: 3 donors, 2 samples per donor | |
|---|---|
| Source | Whole abdominal human skin |
| Thickness | 1.00-1.93 mm |
| Age | 40-51 years. |
| Franz cells | 2 cm² |
| Receiving liquid volume | 3 ml of PBS containing 0.02% Tween 20 |
| Barrier function | Evaluated by determination of insensible water loss, acceptable unless contraindication |
| Formulations | |
| Reference gel containing 100 µg/g compound A* (see composition below**) | Gel containing 100 µg/g dispersed compound A* (Example 2) |
| Gel containing 500 µg/g dispersed compound A* (Example 9) | |

| Application | |
|---|---|
| Application | ~2 mg/cm² |
| Amount of active agent applied | 150~1500 ng/cm² (depending on the dose) |
| Exposure time | 16 h |
| Samples taken up | |
| Washing of donor compartment | ⎫ "Excess"/Dose not absorbed ⎫ |
| Kleenex (for removing the surplus product) | ⎬ ⎬ Balance of masses |
| 1st strip | ⎭ ⎪ |
| Stratum corneum (2-15 strips max) | ⎫ ⎪ |
| Epidermis | ⎬ Total Skin ⎬ Total penetration |
| Dermis | ⎭ ⎪ |
| Receiving Liquid | } Dose absorbed ⎭ |

*Compound A = 3"-tert-butyl-4'-(2-hydroxyethoxy)-4"-pyrrolidin-1-yl-[1,1'; 3',1"]-terphenyl-4-carboxylic acid

**Composition of the reference gel = propylene glycol (30.00%); ethanol 95-96% (67.99%); Klucel HF Pharma (2.00%); compound A (0.01%)

The bioanalysis was carried out by positive electrospray ionization tandem mass spectrometry, and using a Xevo machine (Waters).

The technical conditions are given in the table below.

| | | | | | | |
|---|---|---|---|---|---|---|
| LC column | Hypersil gold 50 × 2.1 mm (UPLC) | | | | | |
| Mobile Phase | Phase A: ACN + 0.1% Formic acid | | | | | |
| | Phase B: $H_2O$ + 0.1% Formic acid | | | | | |
| Washing of needle | ACN | | | | | |
| Washing of septum | ACN/$H_2O$ (50:50) | | | | | |

| | Time (min) | flow rate | % A | % B | Curve |
|---|---|---|---|---|---|
| Gradient | 1. Initial | 0.700 | 15.0 | 85.0 | 0 |
| | 2. 2.5 | 0.700 | 90.0 | 10.0 | 6 |
| | 3. 3.20 | 0.700 | 90.0 | 10.0 | 6 |
| | 4. 3.25 | 0.700 | 15.0 | 85.0 | 6 |

| | ESI + MRM (Positive Electrospray) | | | | |
|---|---|---|---|---|---|
| | Reaction Channel | Dwell (sec) | Voltage (cone) | Col. Energy | Tr (min) | Compound |
| MS/MS Detection | 1: 460.26 > 318.20 | 0.100 | 50.0 | 40.0 | 1.58 | Compound A |
| | 1: 464.06 > 372.10 | 0.100 | 55.0 | 40.0 | 1.58 | Standard Internal Deuterated |

| Injection Volume | 5 µL |
|---|---|
| Run time | 4 minutes |

The quantification limit for compound A is 0.5 ng/mL. The LC/MS/MS conditions developed made it possible to detect up to 0.1% of the dose applied in each of the compartments (dose not absorbed, stratum, epidermis, dermis and receiving liquid). The appropriateness, accuracy and repeatability of the method were checked in each of the matrices, and made it possible to validate the bioanalysis method.

In this type of "single point" study, the parameters retained are:
a. the distribution profile in the various compartments (qualitative data)
b. the penetration into the epidermis+dermis compartment (numerical data)
a. Distribution Profile in the Various Compartments: See FIG. 5

The distribution between the various compartments is of the same type for the 3 formulae evaluated: accumulation in the stratum corneum, lower degree of penetration into the epidermis and very low penetration into the dermis. Compound A is not detected in the receiving liquid. The penetration of compound A from a dispersed gel is lower for an equivalent dose than the reference gel. When the concentration of dispersed compound A is increased to 500 μg/g in the gel, the penetration levels tend to be similar to those obtained after application of the reference gel. The dispersion of compound A in a gel thus makes it possible to minimize the degree of penetration.

b. Values for Penetration into the Epidermis+Dermis Compartment:

The penetration values for the gel containing 100 μg/g (0.01%) of dispersed compound A are about 0.60 ng/cm².

The penetration of compound A after application of the dispersed gel containing 500 μg/g (0.05%) is about 3.45 ng/cm².

This study shows that, for a pharmaceutical composition in the form of a homogeneous suspension of an active principle of the retinoid class in an aqueous gel comprising an effective amount of hydrophobic silica, the amount of active principle that has penetrated into the epidermis and the dermis 16 hours after topical application represents between 0.1% and 0.8% of the applied amount and preferentially between 0.2% and 0.4% of the applied amount.

5—Example 11

Study of Cutaneous Tolerance in Mini-Pigs

Methodology:

4 male and 4 female approximately 4-month-old Göttingen® mini-pigs are included in each study. Each animal is treated daily on the flanks (7 days a week for 4 consecutive weeks) by application of about 17.8 mg/cm² of formulation onto a delimited area. After application, the treated areas are protected until the evaluation of the skin reactions about 6 hours after treatment, via the Draize scale described in the regulatory text "OCDE Guideline No. 404. Acute dermal irritation/corrosion".

| Formation of erythema and sloughing | |
|---|---|
| No erythema | 0 |
| Very mild erythema (barely perceptible) | 1 |
| Well-defined erythema | 2 |

-continued

| Formation of erythema and sloughing | |
|---|---|
| Moderate to serious erythema | 3 |
| Serious erythema (violet-red) with formation of sloughing preventing the rating of the erythema | 4 |

| Formation of edema | |
|---|---|
| No edema | 0 |
| Very mild edema (barely perceptible) | 1 |
| Mild edema (periphery of the edematous area well delimited by distinct swelling) | 2 |
| Moderate edema (swelling of about 1 mm) | 3 |
| Serious edema (swelling of more than 1 mm extending beyond the exposed area) | 4 |

For each formulation, a daily irritancy index (Mean Daily Index or DO, a weekly irritancy index (Mean Weekly Index or WI) and a cumulative irritancy index (Mean Cumulative Irritancy Index or MCII) are calculated.

The formulations are classified according to their irritancy score in the following manner:

| Weekly index (WI) or cumulative index (MCI) | |
|---|---|
| 0 | Non-irritant |
| 0.5 ≥ WI or MCI > 0 | Virtually non-irritant |
| 2 ≥ WI or MCI > 0.5 | Sparingly irritant |
| 5 ≥ WI or MCI > 2 | Irritant |
| 8 ≥ WI or MCI > 5 | Highly irritant |

Results:
1. Tolerance of Formula of Example 1: See FIG. 6

| | Weekly index (WI) | | | | Cumulative index |
|---|---|---|---|---|---|
| Formulation name | W 1 | W 2 | W 3 | W 4 | (MCI) |
| Zorac ® gel 0.05% (Tazarotene 0.05%) | 0.30 | 1.52 | 2.95 | 3.09 | 1.96 |
| Reference gel containing 100 μg/g compound A* (see composition below**) | 0.05 | 0.77 | 2.14 | 2.29 | 1.31 |
| Example 1 containing 100 μg/g compound A* | 0.00 | 0.09 | 0.45 | 0.63 | 0.29 |

*Compound A = 3"-tert-butyl-4'-(2-hydroxyethoxy)-4"-pyrrolidin-1-yl-[1,1'; 3',1"]-terphenyl-4-carboxylic acid
**Composition of the reference gel = propylene glycol (30.00%); ethanol 95-96% (67.99%); Klucel HF Pharma (2.00%); compound A (0.01%)

CONCLUSION

Example 1 is classed as being "virtually non-irritant" and shows better tolerance than the reference gel at the same concentration and than Zorac® gel 0.05%.

The invention claimed is:
1. A pharmaceutical composition comprising
a) an active principle retinoid, which is 3"-tert-butyl-4'-(2-hydroxyeth)-4"-pyrrolidin-1-yl-[1,1';3',1"]-terphenyl-4-carboxylic acid;
b) at least one gelling agent;
c) at least one hydrophobic silica; and
d) water.

2. The composition as claimed in claim 1, wherein the active principle retinoid is in dispersed form.

3. The composition as claimed in claim 1, wherein the hydrophobic silica has a BET surface area from 100 to 260 m$^2$/g.

4. The composition as claimed in claim 1, wherein the gelling agent is selected from the group consisting of polymers of plant origin, gums, pectins, cellulose, polymers of microbiological origin, and gelling polymers of synthetic origin.

5. The composition as claimed in claim 1, wherein the composition also comprises at least one preserving agent.

6. The composition as claimed in claim 5, wherein the preserving agent is selected from the group consisting of methyl paraben, propyl paraben, benzalkonium chloride, phenoxyethanol, benzyl alcohol, potassium sorbate, benzoic acid, 2-bromo-2-nitropropane-1,3-diol, chlorhexidine, chlorocresol, ethyl alcohol and diazolidinylurea.

7. The composition as claimed in claim 1, wherein the composition is provided in the form of a medicament.

8. The composition as claimed in claim 4, wherein the polymer of microbiological origin is xanthan gum.

9. The composition as claimed in claim 1, wherein the gelling agent is selected from the group consisting of:
   acrylate/C10-30 alkyl acrylate crosspolymers,
   polyacrylamides,
   a polyacrylamide/isoparaffin C13-14/laureth-7 mixture,
   carbomers,
   polysaccharides,
   aluminum magnesium silicates,
   acrylic polymers coupled to hydrophobic chains,
   modified starches,
   carrageenans, and
   mixtures thereof.

10. The composition as claimed in claim 9, wherein the polyacrylamide is a sodium acrylamide/acryloyldimethyl taurate copolymer/isohexadecane/polysorbate 80 mixture.

11. The composition as claimed in claim 9, wherein the polysaccharides are selected from the group consisting of xanthan gum, gellan gum, guar gum, and cellulose.

12. The composition as claimed in claim 11, wherein the cellulose is selected from the group consisting of microcrystalline cellulose, sodium carboxymethylcellulose, hydroxypropylmethylcellulose, hydroxyethylcellulose, and sodium carboxymethylcellulose.

13. The composition as claimed in claim 9, wherein the acrylic polymer coupled to hydrophobic chains is the PEG-150/decyl/SMDI copolymer.

14. The composition as claimed in claim 9, wherein the modified starch is a modified potato starch.

15. The composition as claimed in claim 9, wherein the carageenans are divided into four major families: κ, λ, β, ω.

16. A pharmaceutical composition in the form of a homogeneous suspension of an active principle retinoid, which is 3"-tert-butyl-4'-(2-hydroxyethoxy)-4"-pyrrolidin-1-yl-[1,1'; 3',1"]-terphenyl-4-carboxylic acid, in an aqueous gel comprising an effective amount of hydrophobic silica, in which composition the amount of active principle that has penetrated into the epidermis and the dermis 16 hours after topical application represents from 0.1% to 0.8% by weight of the applied dose.

17. The pharmaceutical composition of claim 16, wherein the amount of the active principle retinoid that has penetrated into the epidermis and the dermis 16 hours after topical application is from 0.2% to 0.4% by weight of the applied amount.

18. A pharmaceutical composition in the form of a homogeneous suspension of an active principle retinoid, which is 3"-tert-butyl-4'-(2-hydroxyethoxy)-4"-pyrrolidin-1-yl-[1, 1';3',1"]-terphenyl-4-carboxylic acid, in an aqueous gel comprising an effective amount of hydrophobic silica, for which composition the cumulative irritancy index is less than 1.5.

19. The pharmaceutical composition of claim 18, wherein the cumulative irritancy index is less than 0.5.

20. A process for preparing a pharmaceutical composition according to claim 1, the process comprising the following steps:
   a) adding from 20% to 80% by weight of the total amount of the gelling agent to the total amount of water;
   b) premixing in the solid state the active principle retinoid with at least one hydrophobic silica;
   c) adding, at room temperature and with homogenization, the premix obtained in step b) to the liquid gel obtained in step a); and
   d) adding, with homogenization, the remaining amount of gelling agent to the medium obtained in step c).

21. The process as claimed in claim 20, wherein a lipophilic non-solvent for the active principle retinoid is added in step b).

22. A method of treating a dermatological pathology, the method comprising administering to an individual subject in need thereof an effective amount of the composition as claimed in claim 1, wherein the dermatological pathology is selected from the group consisting of:
   1) common acne, comedonal acne, polymorphic acne, acne rosacea, nodulocystic acne, acne conglobata, senile acne, secondary acne, acne medicamentosa or occupational acne;
   2) ichthyosis, ichthyosiform conditions, lamellar ichthyosis, Darier's disease, palmoplantar keratoderma, leukoplakia, pityriasis rubra pilaris and leukoplakiform conditions, cutaneous or mucosal (buccal) lichen;
   3) dermatological conditions with an inflammatory immunoallergic component;
   4) skin disorders caused by exposure to UV radiation, photo-induced or chronological skin aging, actinic keratoses and pigmentations, or actinic aging;
   5) conditions associated with benign dermal or epidermal proliferations;
   6) immune dermatoses, bullous immune diseases or collagen diseases;
   7) stigmata of epidermal and/or dermal atrophy induced by local or systemic corticosteroids, or cutaneous atrophy;
   8) cicatrization disorders, or stretch marks;
   9) a condition of fungal origin at the cutaneous level;
   10) pigmentation disorders; and
   11) cutaneous or mucosal cancerous or precancerous conditions.

23. The method of claim 22, wherein the dermatological condition with an inflammatory immunoallergic component is selected from cutaneous, mucosal or ungual psoriasis, psoriatic arthritis, atopic dermatitis or various forms of eczema.

24. The method of claim 22, wherein the condition associated with benign dermal or epidermal proliferations is selected from common warts, flat warts, molluscum contagiosum, epidermodysplasia verruciform is, oral papillomatoses or florid papillomatoses.

25. The method of claim 22, wherein the immune dermatosis is lupus erythematosus.

26. The method of claim 22, wherein the collagen disease is scleroderma.

27. The method of claim 22, wherein the condition of fungal origin is tinea pedis or tinea versicolor.

28. The method of claim 22, wherein the pigmentation disorder is selected from hyperpigmentation, melasma, hypopigmentation or vitiligo.

29. The method of claim 22, wherein the cutaneous or mucosal cancerous or precancerous condition is selected from actinic keratoses, Bowen's disease, in-situ carcinomas, keratoacanthomas and skin cancers.

30. The method of claim 29, wherein the skin cancer is basal cell carcinoma (BCC), squamous cell carcinoma (SCC) or a cutaneous lymphoma.

31. The method of claim 30, wherein the cutaneous lymphoma is T lymphoma.

* * * * *